(12) United States Patent
Watanabe et al.

(10) Patent No.: US 8,581,022 B2
(45) Date of Patent: Nov. 12, 2013

(54) METHOD OF IDENTIFYING A COMPOUND FOR PREVENTING AND/OR TREATING AN AUTOIMMUNE DISEASE

(75) Inventors: Norihiko Watanabe, Chiba (JP); Yoshihiro Oya, Chiba (JP)

(73) Assignee: National University Corporation Chiba University, Chiba (JP)

( * ) Notice: Subject to any disclaimer, the term of this patent is extended or adjusted under 35 U.S.C. 154(b) by 132 days.

(21) Appl. No.: 12/749,593

(22) Filed: Mar. 30, 2010

(65) Prior Publication Data
US 2011/0004953 A1 Jan. 6, 2011

Related U.S. Application Data

(60) Provisional application No. 61/222,220, filed on Jul. 1, 2009.

(51) Int. Cl.
*A01K 67/00* (2006.01)
*C12Q 1/02* (2006.01)

(52) U.S. Cl.
USPC .................................. 800/18; 435/29

(58) Field of Classification Search
None
See application file for complete search history.

(56) References Cited

PUBLICATIONS

Miller et al. (J. Immunol. Published online Jun. 17, 2009; 183: 32-36).*
Iwata et al., "Protective Roles of B and T Lymphocyte Attenuator in NKT Cell-Mediated Experimental Hepatitis," The Journal of Immunology, 2010, 184:pp. 127-133.

* cited by examiner

*Primary Examiner* — Scott Long
(74) *Attorney, Agent, or Firm* — Kilyk & Bowersox, P.L.L.C.

(57) ABSTRACT

A method of identifying a compound for preventing and/or treating an autoimmune disease is described which comprises obtaining a ($BTLA^{-/-}$) NKT cell from a non-human animal, contacting the ($BTLA^{-/-}$) NKT cell ex vivo with a test compound, in the presence of an antigen, measuring a response of the ($BTLA^{-/-}$) NKT cell to the antigen, comparing the response of the ($BTLA^{-/-}$) NKT cell to the antigen with a response of a ($BTLA^{-/-}$) NKT cell in control assay, and selecting the compound that reduces the response of the ($BTLA^{-/-}$) NKT cell in the presence of an antigen compared to a response of a ($BTLA^{-/-}$) NKT cell in the control assay. Other methods of identifying a compound for preventing and/or treating an autoimmune disease are also described.

10 Claims, 14 Drawing Sheets

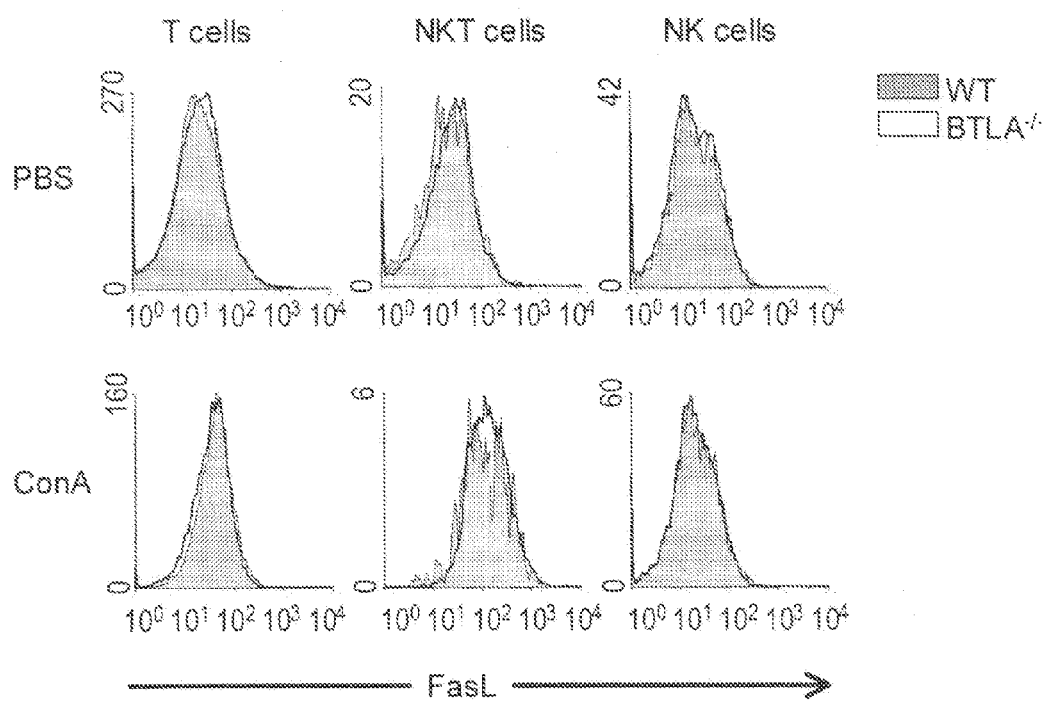

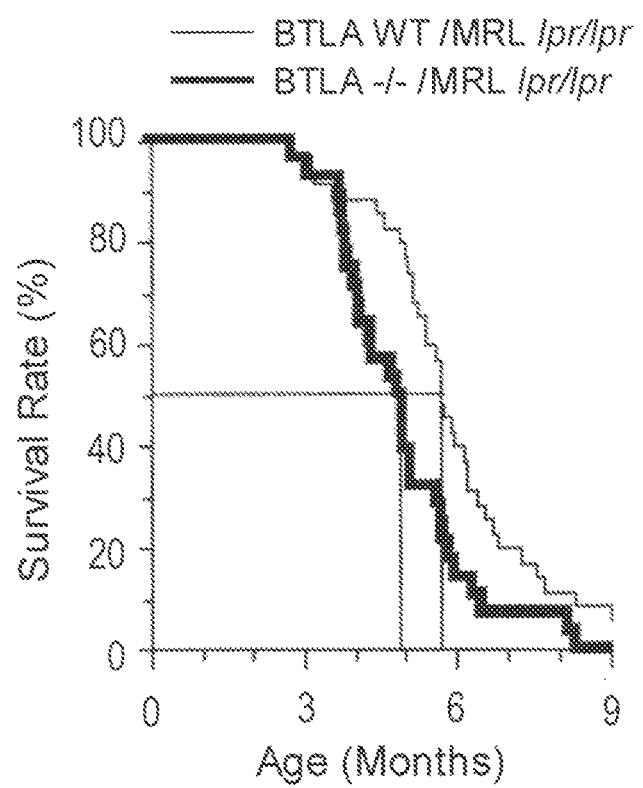

METHOD OF IDENTIFYING A COMPOUND FOR PREVENTING AND/OR TREATING AN AUTOIMMUNE DISEASE

BACKGROUND OF THE INVENTION

This application claims the benefit under 35 U.S.C. §119 (e) of prior U.S. Provisional Patent Application No. 61/222,220, filed Jul. 1, 2009, which is incorporated in its entirety by reference herein.

The present invention relates to methods for preventing various immune responses, and more particularly, relates to methods for preventing autoimmune disease.

Signals delivered through stimulatory and inhibitory co-receptors regulate lymphocyte activation in collaboration with primary antigen-receptor signals. Stimulatory co-receptors include CD28 and inducible T-cell costimulator (ICOS), whereas inhibitory co-receptors include cytotoxic T lymphocyte antigen 4 (CTLA-4), programmed cell death 1 (PD-1), and B and T lymphocyte attenuator (BTLA) (1, 2). Accumulating evidence indicates that the balance between stimulatory and inhibitory co-signals is crucial not only for the effective immune responses to pathogens but also for the maintenance of self-tolerance (1, 2). BTLA has originally been identified as an inhibitory co-receptor selectively expressed on Th1 cells and B cells (3). Thereafter, flow cytometric analyses using monoclonal antibodies against BTLA have revealed that BTLA is expressed on certain lymphocyte subsets including γδ T cells and regulatory T cells as well as on some antigen-presenting cells (APCs) such as macrophages and dendritic cells (DCs) (4, 5). BTLA has also been reported to be expressed at low levels on NK cells (4, 6). More recently, it has been shown that a TNFR family member herpesvirus entry mediator (HVEM) is a ligand for BTLA (5, 7, 8) and that the ligation of BTLA with HVEM transduces inhibitory co-signals (5).

While B and T lymphocyte attenuator (BTLA) was originally identified as an inhibitory co-receptor selectively expressed on Th1 cells and B cells, recent studies have revealed that BTLA is expressed on a variety of cells including macrophages, dendritic cells, and NK cells and modulates their functions. However, the role of BTLA in the regulation of NKT cell function remains unknown.

In vivo function of BTLA has recently been addressed using BTLA-deficient (BTLA$^{-/-}$) mice. Initially, the present inventors found that the sensitivity to experimental autoimmune encephalomyelitis (EAE) as well as T cell-dependent antibody responses is increased in BTLA$^{-/-}$ mice (3). It has also been reported that BTLA$^{-/-}$ mice exhibit a rapid rejection of partially MHC-mismatched cardiac allograft (9), persistent allergic airway inflammation following antigen challenge (10, 11), and an acceleration of experimental colitis (12). These findings indicate that BTLA is crucial for dampening immune responses mediated by T cells. Moreover, the present inventors have found that aged BTLA$^{-/-}$ mice spontaneously develop autoimmune hepatitis-like disease with an increase of NKT cells in the liver (13), suggesting that BTLA may prevent autoimmune hepatitis through the inhibition of NKT cell function.

NKT are characterized by co-expression of T cell markers such as T cell receptor (TCR) and NK cell markers such as NK1.1 (14). In mice, the majority of NKT cells expresses an invariant Vα14 TCR, which is essential for their development (14), and recognizes a specific ligand, α-galactosylceramide (α-GalCer), presented on CD1d molecules (14, 15). NKT cells rapidly produce both IL-4 and IFN-γ upon activation (15, 16) and play a crucial role in various immune responses, including anti-tumor immunity, allergic reaction, and autoimmune diseases (14). While the roles of stimulatory co-receptors in NKT cell function have been addressed (17, 18), the role of inhibitory co-receptors including BTLA in NKT cell function remains largely unknown.

REFERENCES

1. Greenwald, R. J., G. J. Freeman, and A. H. Sharpe. 2005. The B7 family revisited. *Annu Rev Immunol* 23:515-548.
2. Watts, T. H. 2005. TNF/TNFR family members in costimulation of T cell responses. *Annu Rev Immunol* 23:23-68.
3. Watanabe, N., M. Gavrieli, J. R. Sedy, J. Yang, F. Fallarino, S. K. Loftin, M. A. Hurchla, N. Zimmerman, J. Sim, X. Zang, T. L. Murphy, J. H. Russell, J. P. Allison, and K. M. Murphy. 2003. BTLA is a lymphocyte inhibitory receptor with similarities to CTLA-4 and PD-1. *Nat Immunol* 4:670-679.
4. Han, P., O. D. Goularte, K. Rufner, B. Wilkinson, and J. Kaye. 2004. An inhibitory Ig superfamily protein expressed by lymphocytes and APCs is also an early marker of thymocyte positive selection. *J Immunol* 172:5931-5939.
5. Murphy, K. M., C. A. Nelson, and J. R. Sedy. 2006. Balancing co-stimulation and inhibition with BTLA and HVEM. *Nat Rev Immunol* 6:671-681.
6. Hurchla, M. A., J. R. Sedy, M. Gavrieli, C. G. Drake, T. L. Murphy, and K. M. Murphy. 2005. B and T lymphocyte attenuator exhibits structural and expression polymorphisms and is highly Induced in anergic CD4+T cells. *J Immunol* 174:3377-3385.
7. Gonzalez, L. C., K. M. Loyet, J. Calemine-Fenaux, V. Chauhan, B. Wranik, W. Ouyang, and D. L. Eaton. 2005. A coreceptor interaction between the CD28 and TNF receptor family members B and T lymphocyte attenuator and herpesvirus entry mediator. *Proc Natl Acad Sci USA* 102:1116-1121.
8. Sedy, J. R., M. Gavrieli, K. G. Potter, M. A. Hurchla, R. C. Lindsley, K. Hildner, S. Scheu, K. Pfeffer, C. F. Ware, T. L. Murphy, and K. M. Murphy. 2005. B and T lymphocyte attenuator regulates T cell activation through interaction with herpesvirus entry mediator. *Nat Immunol* 6:90-98.
9. Tao, R., L. Wang, R. Han, T. Wang, Q. Ye, T. Honjo, T. L. Murphy, K. M. Murphy, and W. W. Hancock. 2005. Differential effects of B and T lymphocyte attenuator and programmed death-1 on acceptance of partially versus fully MHC-mismatched cardiac allografts. *J Immunol* 175:5774-5782.
10. Deppong, C., T. I. Juehne, M. Hurchla, L. D. Friend, D. D. Shah, C. M. Rose, T. L. Bricker, L. P. Shornick, E. C. Crouch, T. L. Murphy, M. J. Holtzman, K. M. Murphy, and J. M. Green. 2006. Cutting edge: B and T lymphocyte attenuator and programmed death receptor-1 inhibitory receptors are required for termination of acute allergic airway inflammation. *J Immunol* 176:3909-3913.
11. Tamachi, T., N. Watanabe, Y. Oya, S. Kagami, K. Hirose, Y. Saito, I. Iwamoto, and H. Nakajima. 2007. B and T lymphocyte attenuator inhibits antigen-induced eosinophil recruitment into the airways. *Int Arch Allergy Immunol* 143 Suppl 1:50-55.
12. Steinberg, M. W., O. Turovskaya, R. B. Shaikh, G. Kim, D. F. McCole, K. Pfeffer, K. M. Murphy, C. F. Ware, and M. Kronenberg. 2008. A crucial role for HVEM and BTLA in preventing intestinal inflammation. *J Exp Med* 205:1463-1476.
13. Oya, Y., N. Watanabe, T. Owada, M. Oki, K. Hirose, A. Suto, S. Kagami, H. Nakajima, T. Kishimoto, I. Iwamoto, T. L. Murphy, K. M. Murphy, and Y. Saito. 2008. Development of autoimmune hepatitis-like disease and production of autoantibodies to nuclear antigens in mice lacking B and T lymphocyte attenuator. *Arthritis Rheum* 58:2498-2510.
14. Taniguchi, M., M. Harada, S. Kojo, T. Nakayama, and H. Wakao. 2003. The regulatory role of Valpha14 NKT cells in innate and acquired immune response. *Annu Rev Immunol* 21:483-513.
15. Kawano, T., J. Cui, Y. Koezuka, I. Toura, Y. Kaneko, K. Motoki, H. Ueno, R. Nakagawa, H. Sato, E. Kondo, H. Koseki, and M. Taniguchi. 1997. CD1d-restricted and TCR-mediated activation of valpha14 NKT cells by glycosylceramides. *Science* 278:1626-1629.
16. Chen, H., and W. E. Paul. 1997. Cultured NK1.1+ CD4+ T cells produce large amounts of IL-4 and IFN-gamma upon activation by anti-CD3 or CD1. *J Immunol* 159:2240-2249.
17. Ikarashi, Y., R. Mikami, A. Bendelac, M. Terme, N. Chaput, M. Terada, T. Tursz, E. Angevin, F. A. Lemonnier, H. Wakasugi, and L. Zitvogel. 2001. Dendritic cell maturation overrules H-2D-mediated natural killer T (NKT) cell inhibition: critical role for B7 in CD1d-dependent NKT cell interferon gamma production. *J Exp Med* 194:1179-1186.
18. Kaneda, H., K. Takeda, T. Ota, Y. Kaduka, H. Akiba, Y. Ikarashi, H. Wakasugi, M. Kronenberg, K. Kinoshita, H. Yagita, and K. Okumura. 2005. ICOS costimulates invariant NKT cell activation. *Biochem Biophys Res Commun* 327:201-207.
19. Kaneko, Y., M. Harada, T. Kawano, M. Yamashita, Y. Shibata, F. Gejyo, T. Nakayama, and M. Taniguchi. 2000. Augmentation of Valpha14 NKT cell-mediated cytotoxicity by interleukin 4 in an autocrine mechanism resulting in the development of concanavalin A-induced hepatitis. *J Exp Med* 191:105-114.
20. Takeda, K., Y. Hayakawa, L. Van Kaer, H. Matsuda, H. Yagita, and K. Okumura. 2000. Critical contribution of liver natural killer T cells to a murine model of hepatitis. *Proc Natl Acad Sci USA* 97:5498-5503.
21. Cui, J., T. Shin, T. Kawano, H. Sato, E. Kondo, I. Toura, Y. Kaneko, H. Koseki, M. Kanno, and M. Taniguchi. 1997. Requirement for Valpha14 NKT cells in IL-12-mediated rejection of tumors. *Science* 278:1623-1626.
22. Watarai, H., R. Nakagawa, M. Omori-Miyake, N. Dashtsoodol, and M. Taniguchi. 2008. Methods for detection, isolation and culture of mouse and human invariant NKT cells. *Nat Protoc* 3:70-78.
23. Tiegs, G., J. Hentschel, and A. Wendel. 1992. A T cell-dependent experimental liver injury in mice inducible by concanavalin A. *J Clin Invest* 90:196-203.
24. Mizuhara, H., E. O'Neill, N. Seki, T. Ogawa, C. Kusunoki, K. Otsuka, S. Satoh, M. Niwa, H. Senoh, and H. Fujiwara. 1994. T cell activation-associated hepatic injury: mediation by tumor necrosis factors and protection by interleukin 6. *J Exp Med* 179:1529-1537.
25. Mizuhara, H., M. Uno, N. Seki, M. Yamashita, M. Yamaoka, T. Ogawa, K. Kaneda, T. Fujii, H. Senoh, and H. Fujiwara. 1996. Critical involvement of interferon gamma in the pathogenesis of T-cell activation-associated hepatitis and regulatory mechanisms of interleukin-6 for the manifestations of hepatitis. *Hepatology* 23:1608-1615.
26. Louis, H., O. Le Moine, M. O. Peny, E. Quertinmont, D. Fokan, M. Goldman, and J. Deviere. 1997. Production and role of interleukin-10 in concanavalin A-induced hepatitis in mice. *Hepatology* 25:1382-1389.
27. Ajuebor, M. N., C. M. Hogaboam, T. Le, and M. G. Swain. 2003. C-C chemokine ligand 2/monocyte chemoattractant protein-1 directly inhibits NKT cell IL-4 production and is hepatoprotective in T cell-mediated hepatitis in the mouse. *J Immunol* 170:5252-5259.
28. Chang, W. S., J. Y. Kim, Y. J. Kim, Y. S. Kim, J. M. Lee, M. Azuma, H. Yagita, and C. Y. Kang. 2008. Cutting edge: Programmed death-1/programmed death ligand 1 interaction regulates the induction and maintenance of invariant NKT cell anergy. *J Immunol* 181:6707-6710.
29. Wang, Y., S. K. Subudhi, R. A. Anders, J. Lo, Y. Sun, S. Blink, Y. Wang, J. Wang, X. Liu, K. Mink, D. Degrandi, K. Pfeffer, and Y. X. Fu. 2005. The role of herpesvirus entry mediator as a negative regulator of T cell-mediated responses. *J Clin Invest* 115:711-717.
30. Anand, S., P. Wang, K. Yoshimura, I. H. Choi, A. Hilliard, Y. H. Chen, C. R. Wang, R. Schulick, A. S. Flies, D. B. Flies, G. Zhu, Y. Xu, D. M. Pardoll, L. Chen, and K. Tamada. 2006. Essential role of TNF family molecule LIGHT as a cytokine in the pathogenesis of hepatitis. *J Clin Invest* 116:1045-1051.

SUMMARY OF THE INVENTION

A feature of the present invention is to provide a method for identifying a compound for inhibiting or reducing NKT cell function.

Another feature of the present invention to provide a method for identifying a compound for inhibiting or reducing the immune response of NKT cells which lack at least a part of BTLA gene.

An additional feature of the present invention is to provide a method for identifying a compound for treating an autoimmune disease.

A further feature of the present invention is to provide a method for identifying a compound for preventing an autoimmune disease.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a method of identifying a compound for preventing and/or treating an autoimmune disease. For instance, one method includes obtaining a ($BTLA^{-/-}$) NKT cell from a non-human animal, contacting the ($BTLA^{-/-}$) NKT cell ex vivo with a test compound, in the presence of an antigen, measuring a response of the ($BTLA^{-/-}$) NKT cell to the antigen, and comparing the response of the ($BTLA^{-/-}$) NKT cell to the antigen with a response of a ($BTLA^{-/-}$) NKT cell in a control assay, and selecting the compound that reduces the response of the ($BTLA^{-/-}$) NKT cell in the presence of an antigen compared to a response of the ($BTLA^{-/-}$) NKT cell in the control assay.

The present invention, in addition, relates to a method of identifying a compound that inhibits, reduces, or attenuates the response of a ($BTLA^{-/-}$) NKT cell in the presence of an antigen. Other methods are further described.

It is to be understood that both the foregoing general description and the following detailed description are exemplary and explanatory only and are intended to provide a further explanation of the present invention, as claimed.

BRIEF DESCRIPTION OF DRAWINGS

FIG. 4 D shows levels of TNF-α, IFN-γ, and IL-4. Sera were collected at 1, 3, 8, and 24 hours after ConA injection and the levels of TNF-α, IFN-γ, and IL-4 were determined. Data are means±SD, n=4, *p<0.05.

FIG. 6 C shows the numbers of total thymocytes, CD4$^-$CD8$^-$ double-negative cells (DN), CD4$^+$CD8$^+$ double-positive cells (DP), CD4 single-positive cells (CD4), and CD8 single positive-cells (CD8) from 4-month-old BTLA$^{-/-}$ MRL-lpr/lpr mice (filled bars) and littermate BTLA WT MRL-lpr/lpr mice (open bars). Data are mean ±SD for 4 mice in each group. The numbers of total splenocytes, CD4$^+$CD8$^-$ cells (CD4), and CD4$^-$CD8$^+$cells (CD8), CD3ε$^-$B220$^+$ cells (B cell), CD3ε$^+$B220$^+$ cells (lpr cells) are also shown. Pictures shown at the bottom are the representative appearances of the thymus and the spleen of BTLA WT MRL-lpr/lpr mice and BTLA$^{-/-}$ MRL-lpr/lpr mice.

FIGS. 7 E-H show representative photographs of hematoxylin and eosin staining (HE) of lung of 4-month-old BTLA$^{-/-}$ MRL-lpr/lpr mice and BTLA WT MRL-lpr/lpr mice, reflecting exacerbation of inflammatory cell infiltration in multiple organs of BTLA$^{-/-}$ MRL-lpr/lpr mice. Figures G and H show exacerbation of Inflammatory cell infiltration in the peribronchial area of BTLA$^{-/-}$ MRL-lpr/lpr mice.

FIGS. 7 I-L show representative photographs of hematoxylin and eosin staining (HE) of pancreas of 4-month-old BTLA$^{-/-}$ MRL-lpr/lpr mice and BTLA WT MRL-lpr/lpr mice, reflecting exacerbation of inflammatory cell infiltration in multiple organs of BTLA$^{-/-}$ MRL-lpr/lpr mice. Figures K-L show inflammatory cell infiltration around the pancreatic duct of BTLA$^{-/-}$ MRL-lpr/lpr mice.

FIGS. 7 M-P show representative photographs of hematoxylin and eosin staining (HE) of, kidney of 4-month-old BTLA$^{-/-}$ MRL-lpr/lpr mice and BTLA WT MRL-lpr/lpr mice, reflecting exacerbation of inflammatory cell infiltration in multiple organs of BTLA$^{-/-}$ MRL-lpr/lpr mice. Figures O-P show exaggerated lymphocytes inflammation in the interstitial area of kidney in BTLA$^{-/-}$ MRL-lpr/lpr mice.

FIGS. 7 Q-T show representative photographs of hematoxylin and eosin staining (HE) of, joint of 4-month-old BTLA$^{-/-}$ MRL-lpr/lpr mice and BTLA WT MRL-lpr/lpr mice, reflecting exacerbation of inflammatory cell infiltration in multiple organs of BTLA$^{-/-}$ MRL-lpr/lpr mice of 4-month-old BTLA$^{-/-}$ MRL-lpr/lpr mice and BTLA WT MRL-lpr/lpr mice, reflecting exacerbation of inflammatory cell infiltration in multiple organs of BTLA$^{-/-}$ MRL-lpr/lpr mice. Figures S-T show progressed arthritis in the foot joint in BTLA$^{-/-}$ MRL-lpr/lpr mice. Size bar indicates 50 or 500 μm.

FIGS. 9 E-H shows interface hepatitis (piecemeal necrosis) in the liver of BTLA$^{-/-}$ MRL-lpr/lpr mice. FIG. 9E shows low-power photomicrograph of the portal tracts of BTLA$^{-/-}$ MRL lpr/lpr mice. Marked portal inflammation and severe piecemeal necrosis that is continuous around the portal tract (PT) and extends toward the centrilobular vein (CV). FIG. 9F shows high-power photomicrographs of the penetrating mononuclear cell into the periportal hepatic lobule. Figures G and H show hepatic vein indicated with black arrowhead was totally filled with mononuclear cells. White arrowheads in G and H indicate the margin of Glisson's sheath disclosed by silver staining. Note the marked mononuclear cell infiltration in the portal tracts that extends beyond Glisson's sheath and penetrates into the periportal parenchyma (piecemeal necrosis).

FIGS. 9 I and M show hepatocytes around the central veins were severely damaged by infiltrating inflammatory cells.

FIGS. 9 J and N show bile ducts were damaged by severe inflammation in the portal tracts. (K, L, O, P) Endothelialitis in the liver of BTLA$^{-/-}$ MRL-lpr/lpr mice. Subendothelial mononuclear cell infiltration in the wall of a portal vein is shown.

FIGS. 9 O and P show some endothelial cells lift off from the underlying basement membrane of the vein (endothelialitis) (white arrowhead). Size bar indicates 50 or 500 μm.

DETAILED DESCRIPTION OF THE PRESENT INVENTION

Figure 1:
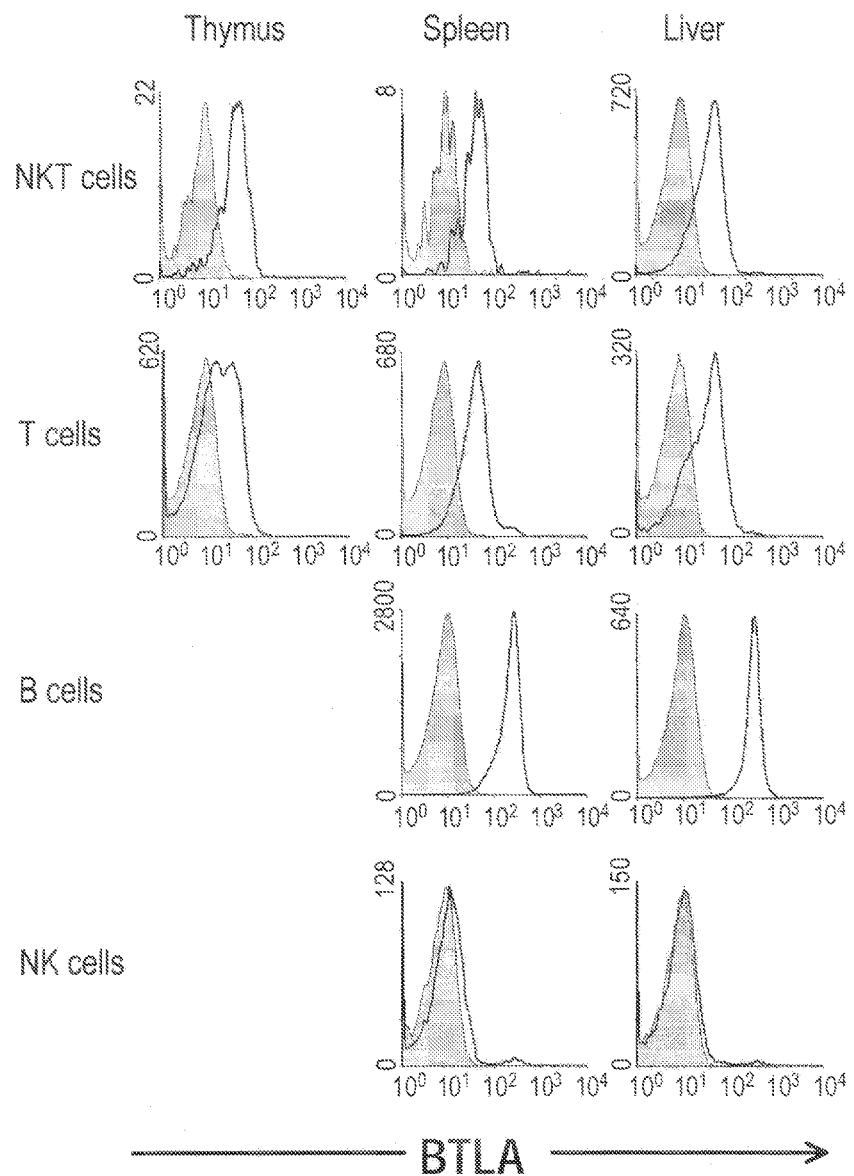
FIG. 1 shows representative histograms of BTLA expression (solid line) on NKT cells (CD3$^+$ α-GalCer/CD1d-dimer$^+$), T cells (CD3$^{high}$ α-GalCer/CD1d-dimer$^-$), B cells (CD3$^-$ B220$^+$), and NK cells (NK1.1$^+$ CD3$^-$), reflecting that BTLA is expressed on NKT cells at levels similar to those on CD3$^+$ T cells. Mononuclear cells from thymus, spleen, and liver in C57BL/6 mice were stained with anti-BTLA mAb. Shaded areas indicate control staining with isotype-matched antibody.

The present invention relates to a method for identifying a compound for preventing and/or treating an autoimmune disease. According to the method of the present invention, a (BTLA$^{-/-}$) NKT cells is obtained from an animal (e.g., mammal). The animal can be a mouse that lacks at least a part of the BTLA gene. The animal can be a MRL lpr/lpr mouse. The method can comprise contacting the (BTLA$^{-/-}$) NKT cell with a test compound in the presence of an antigen, under suitable assay conditions. A response of the (BTLA$^{-/-}$) NKT cell to the antigen can be measured and compared with the antigenic response of a (BTLA$^{-/-}$) NKT cell that is not contacted with the test compound. The response of the (BTLA$^{-/-}$) NKT cell to the antigen can be an increased cytokine production. The response of the (BTLA$^{-/-}$) NKT cell to the antigen can be an increased production of IFN-γ and/or IL-4 by the (BTLA$^{-/-}$) NKT cell. A reduced or attenuated response of the (BTLA$^{-/-}$) NKT cell to the antigen identifies the compound as a therapeutic compound or as a compound for preventing and/or treating an autoimmune disease. The autoimmune disease can be, for example, autoimmune hepatitis and the (BTLA$^{-/-}$) NKT cells can be hepatic (BTLA$^{-/-}$) NKT cells.

The method for identifying a compound for preventing and/or treating an autoimmune disease can alternatively comprise contacting a (BTLA$^{-/-}$) NKT cell with a test compound in the presence of an antigen, under suitable assay conditions. A response of the (BTLA$^{-/-}$) NKT cell to the antigen can be measured and compared with the antigenic response of (BTLA$^{-/-}$) NKT cells that are not contacted with the test compound. If the compound inhibits, reduces or attenuates the response of the (BTLA$^{-/-}$) NKT cell to the antigen, the compound can be administered to an animal. For example, the compound can be administered to a mouse or other mammal. The compound can be administered to an MRL lpr/lpr mouse. A response of the animal to an antigen or substance that causes an autoimmune response can then be measured. If the test compound is found to have reduced the immune response in the mouse compared to an antigenic response of an animal to which a test compound is not administered, the test compound can be identified as a compound for preventing and/or treating the autoimmune disease.

The method for identifying a compound for preventing and/or treating an autoimmune disease can comprise screening for compounds that inhibit or reduce the production of IFN-γ and/or IL-4 produced by (BTLA$^{-/-}$) NKT cells in response to an antigen. According to the method of the present invention, (BTLA$^{-/-}$) NKT cells are obtained from an animal that lacks at least a part of the BTLA gene. The animal can be a mouse. The animal can be a MRL lpr/lpr mouse. The method can include collecting spleen cells from the animal and incubating the spleen cells with α-galactosyl ceramide (α-GalCer). The (BTLA$^{-/-}$) NKT cells can then be incubated with the spleen cells that are derived from the animal and previously incubated with α-galactosyl ceramide (α-GalCer), and then be contacted with a test compound. A control assay can be separately prepared in which the (BTLA$^{-/-}$) NKT cells are incubated with similarly prepared spleen cells, but are not contacted with the test compound. The response of the (BTLA$^{-/-}$) NKT cells to the spleen cells in the presence of the test compound can be measured and compared with the response of the (BTLA$^{-/-}$) NKT cells to the spleen cells in the control assay. A reduced response of the (BTLA$^{-/-}$) NKT cells to the spleen cells in the presence of the test compound can be compared to the response of (BTLA) NKT cells of the control assay. A reduced response of the (BTLA$^{-/-}$) NKT cells that are contacted with the test compound can identify the compound as a compound for preventing and/or treating an autoimmune disease.

Based on the findings described herein, it is believed that BTLA functions as the inhibitory co-receptor in NKT cells and thus prevents NKT cell-mediated tissue damage. After examining the role of BTLA in the regulation of NKT cell function, the present inventors found that BTLA was expressed on NKT cells at levels similar to the levels of expression on T cells. BTLA$^{-/-}$ NKT cells produced larger amounts of IL-4 and IFN-γ upon α-GalCer stimulation as compared with wild-type (WT) NKT cells. Importantly, BTLA$^{-/-}$ mice were highly susceptible to concanavalin A (ConA)-induced hepatitis, in which NKT cells have been reported to play pathogenic roles (19, 20). In vivo, BTLA$^{-/-}$ mice produced larger amounts of IL-4 and IFN-β upon concanavalin A (ConA) injection and were more susceptible to ConA-induced hepatitis than WT mice. The augmentation of ConA-induced hepatitis in BTLA$^{-/-}$ mice was not observed in BTLA/NKT-double deficient mice. It was determined, based on these findings, that compounds that can inhibit or reduce the response of BTLA$^{-/-}$ NKT cells that are exposed to an antigen, could also be used to treat or prevent autoimmune disease.

These results suggest that BTLA functions as the inhibitory co-receptor of NKT cells and plays a critical role in the prevention of autoimmune disease, such as NKT cell-mediated liver injury.

The present inventors found that BTLA is expressed on NKT cells (FIG. 1) and that BTLA$^{-/-}$ NKT cells produce larger amounts of cytokines upon antigen stimulation than WT NKT cells (FIG. 3), suggesting that BTLA exerts inhibitory effects on NKT cells. In addition, it has recently been demonstrated that PD-1/PD-L1 interaction is essential for the induction and maintenance of anergic state of NKT cells (28). It has also been demonstrated that stimulatory co-receptors such as CD28 (17) and ICOS (18) play a significant role in the induction of cytokine production from NKT cells. Taken together, these findings suggest that analogous to T cells, the activation of NKT cells is regulated by the balance between stimulatory co-signals and inhibitory co-signals including BTLA.

Figure 4A:
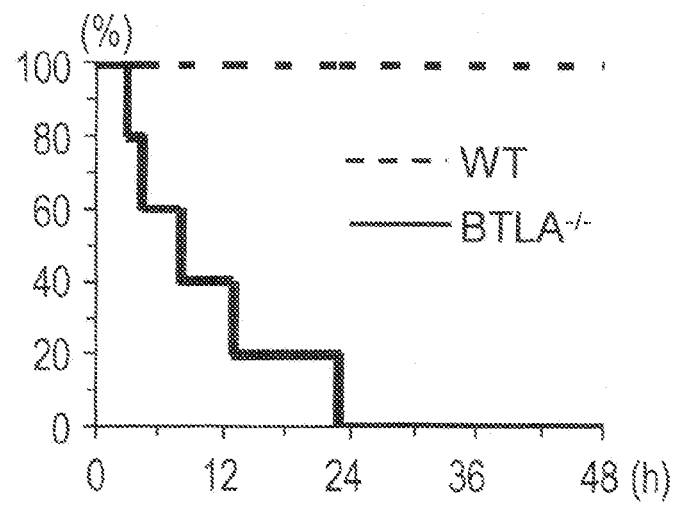
FIG. 4 A shows increased susceptibility to ConA-induced hepatitis in BTLA$^{-/-}$ mice (A) BTLA$^{-/-}$ mice (solid line) and WT mice (dotted line) were injected intravenously with ConA (20 mg/kg) and the survival of the mice was evaluated for 48 hours (n=5). (B-E) BTLA$^{-/-}$ mice and WT mice were injected intravenously with a sublethal dose of ConA (10 mg/kg).
FIG. 4B shows representative photomicrographs (HE staining) of the liver of BTLA$^{-/-}$ mice and WT mice, n=6 mice in each group. The liver was excised at 24 hours after ConA injection.
FIG. 4C shows levels of ALT and AST. Sera were collected at 12 and 24 hours after ConA injection and the levels of ALT and AST were determined Data are means ±SD, n=6, *p<0.05, **p<0.01.
FIG. 4E shows representative histograms for FasL expression on T cells (CD3ε$^+$ α-GalCer/CD1d-dimer$^+$), NKT cells (CD3ε$^+$ α-GalCer/CD1d-dimer$^+$), and NK cells (CD3ε$^-$ NK1.1$^+$) in the liver. n=4. One hour after ConA injection, liver mononuclear cells were isolated and the expression levels of Fas ligand (FasL) were analyzed by flow cytometry.
Figure 4B:
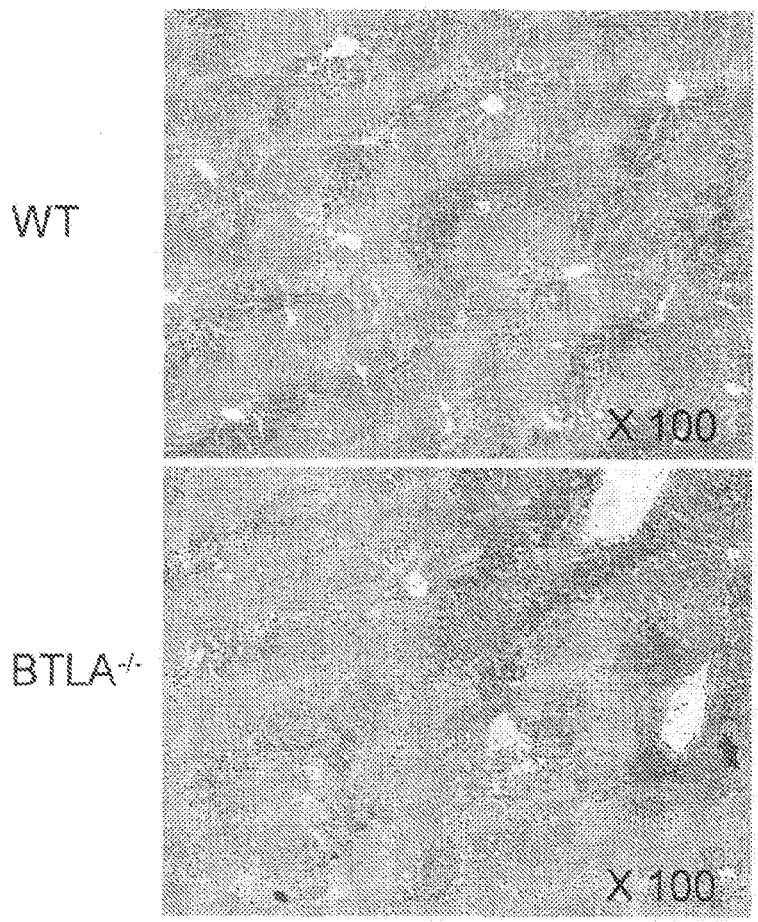
Figure 4C:
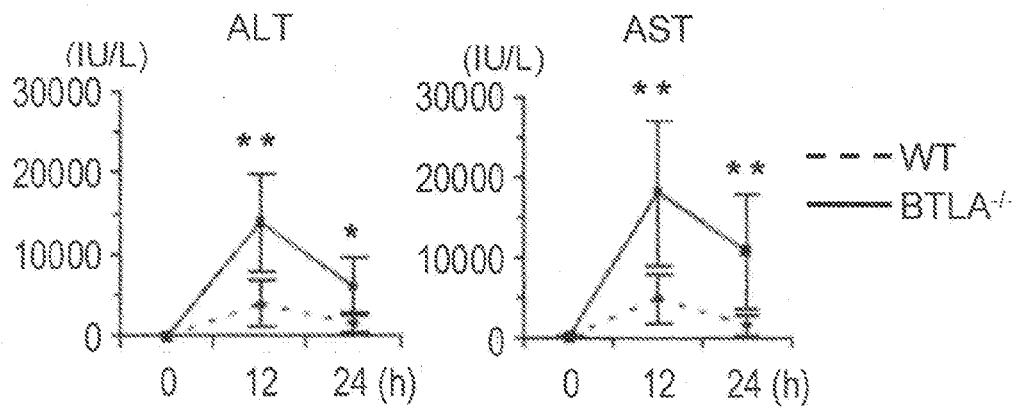
Figure 4D:
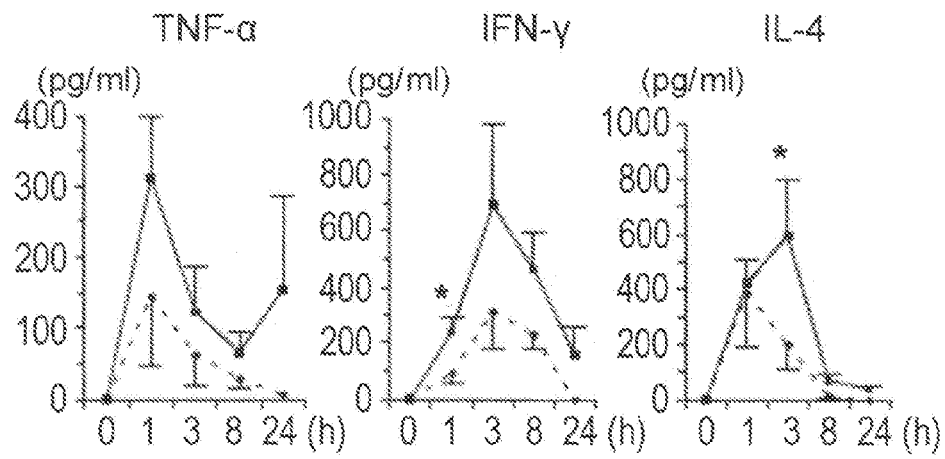
Figure 5:
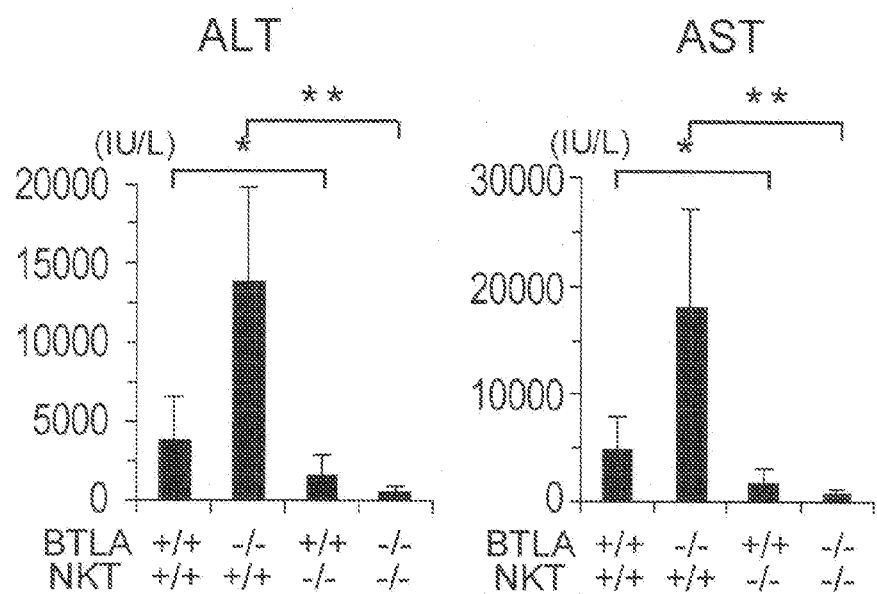
FIG. 5 shows levels of ALT and AST, reflecting that NKT cells are required for the augmentation of ConA-induced hepatitis in BTLA$^{-/-}$ mice. WT mice, BTLA$^{-/-}$ mice, NKT$^{-/-}$ mice (Jα281$^{-/-}$ mice), and BTLA$^{-/-}$ NKT$^{-/-}$ mice were injected intravenously with a sublethal dose of ConA (10 mg/kg). Sera were collected at 12 hours after ConA injection and the levels of ALT and AST were determined. Data are means ±SD, n=6, *p<0.05, **p<0.01.

As depicted in FIG. 4, and further explained below BTLA$^{-/-}$ mice are highly susceptible to ConA-induced hepatitis, in which NKT cells have been shown to play a significant role (19, 20). Indeed, while ConA-induced hepatitis was significantly attenuated in NKT$^{-/-}$ mice as compared with WT mice, the augmentation of ConA-induced hepatitis in BTLA$^{-/-}$ mice was not observed in BTLA$^{-/-}$ NKT$^{-/-}$ mice (FIG. 5). Together, these results indicate that BTLA mediates an inhibitory signal in NKT cells and dampens the activation of NKT cells to abrogate ConA-induced hepatitis. Recently, it has been demonstrated that the mice lacking HVEM, a ligand for BTLA (5, 7, 8), are also highly susceptible to ConA injection to induce increased CD4$^+$ T cell activation but exhibit no significant liver damage (29). Because HVEM is not only a ligand for BTLA but also a costimulatory receptor for LIGHT (5), NKT cell activation might not be sufficient for inducing hepatitis in HVEM-deficient mice. Thus, it is indicated that BTLA-HVEM interaction is involved in the control of pathogenic activation of NKT cells such as ConA-induced hepatitis.

Figure 3:
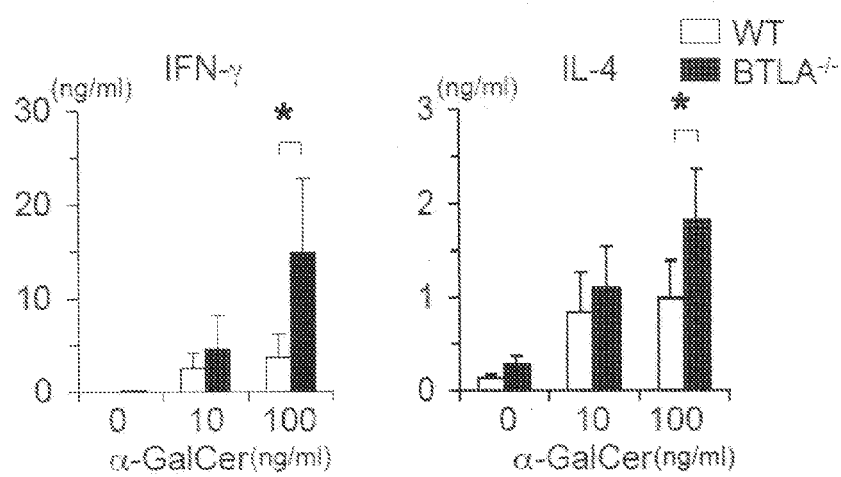
FIG. 3 shows levels of IFN-γ and IL-4, reflecting increased activation of BTLA$^{-/-}$ NKT cells upon antigen receptor stimulation in vitro. NKT cells (5×10$^4$) were purified from the liver of WT and BTLA$^{-/-}$ mice and co-cultured with α-GalCer-loaded irradiated splenocytes (5×10$^4$) as APCs for 36 hours. The levels of IFN-γ and IL-4 in the culture supernatants were measured by ELISA. Data are means ±SD for 6 mice in each group. *p<0.05.

The effector mechanisms by which NKT cells induce ConA-induced hepatitis remain to be elucidated. Previous studies have shown that NKT cell-derived cytokines including IL-4 are crucial for NKT cell-mediated liver injury (19). As shown in FIG. 3 and FIG. 4, not only IL-4 production from α-GalCer-activated NKT cells but also serum levels of IL-4 in ConA-injected mice were enhanced in BTLA$^{-/-}$ mice. On the other hand, FasL expression was similarly upregulated on BTLA$^{-/-}$ NKT cells and WT NKT cells upon ConA injection (FIG. 4E). Thus, it is believed that the elevated levels of cytokines rather than FasL expression might be involved in the augmentation of ConA-induced hepatitis in BTLA$^{-/-}$ mice. In addition, it has recently been suggested that soluble LIGHT released from NKT cells may also be an effector molecule for ConA-induced hepatitis (30).

The present inventors have shown that BTLA functions as an inhibitory co-receptor in NKT cells and prevents NKT cell-mediated experimental hepatitis. Thus, enhancement of BTLA signaling in NKT cells by agonistic ligands or by a stimulatory antibody may be useful for treatment of a number of diseases in which NKT cells play a pathogenic role. Compounds identified by the above-described screening methods can be utilized as inhibitors or antagonists of (BTLA$^{-/-}$) NKT cells. Examples of the aforementioned candidate compounds for the inhibitor or antagonist, can include a protein, a polypeptide, a polypeptide without antigenicity, and a low molecular weight compound. A low molecular weight compound is preferred.

Candidate compounds or test compounds can be selected based on biological usefulness and toxicity and used in pharmaceutical compositions for treating autoimmune disease.

The (BTLA$^{-/-}$) NKT cells can be obtained from a human. Alternatively, the (BTLA$^{-/-}$) NKT cells can be obtained from a non-human animal, such as a mouse. It should be understood, however, that those skilled in the art can readily determine and/or obtain (BTLA$^{-/-}$) NKT cells, and what is the most desirable source of such cells. Additionally, methods of obtaining, storing, culturing, and manipulating cells to ensure the introduction of the minimal amount of irrelevant variations between samples, are well known in the art.

The term "antigen" as used herein refers to any substance that, as a result of coming in contact with the (BTLA$^{-/-}$) NKT cells can induce a response, a state of sensitivity and/or immune responsiveness by the (BTLA$^{-/-}$) NKT cells after a period of time. An antigen can be a substance that causes an autoimmune response.

The term "a cell" is intended to include single cells, as well as pluralities of cells in a cell suspension, cell culture, or tissue sample. The type and number of cells to use to identify a therapeutic compound will depend on the assay used, and can be determined by those skilled in the art for a given application of the method.

As used herein, the term "suitable assay conditions" is intended to mean conditions under which a particular assay will identify a compound. Suitable assay conditions take into account factors such as the concentration of the compound, the duration of contact with the compound, the temperature and buffer conditions, the method of contact, whether or not cell viability is required, and the detection format. Suitable assay conditions can depend on the number of compounds being screened. Assay conditions to identify compounds that alter predetermined properties of cells are known in the art or can be readily determined for a particular application of the method.

EXAMPLES

Example 1

The materials and methods used in Example 1, are described below:

Mice: BTLA-deficient (BTLA$^{-/-}$) mice (3) were backcrossed over 8 generations onto C57BL/6 mice (Charles River Laboratories, Kanagawa, Japan). NKT cell-deficient (NKT$^{-/-}$) mice (Jα281$^{-/-}$ mice) on a C57/BL6 background were described previously (21). NKT mice were crossed with BTLA$^{-/-}$ mice and the offspring were intercrossed to obtain BTLA$^{-/-}$ NKT$^{-/-}$ mice. All mice were housed in microisolator cages under specific pathogen-free conditions and the mice at 6-12 weeks of age were used for the experiments. Animal procedures in this study were approved by the Chiba University Animal Care and Use Committee.

Flow cytometry: The following antibodies were purchased from BD Biosciences (San Diego, Calif.): anti-CD3ε FITC, PE (145-2C11), anti-NK1.1 PE (PK136), anti-CD45R/B220 FITC, PE (RA3-6B2), anti-T cell receptor (anti-TCR) β chain FITC, PE (H57-597), anti-CD8α FITC (53-6.7), anti-CD11b FITC (M1/70), anti-CD11c FITC (HL3), anti-CD25 FITC (7D4), anti-CD69 FITC (H1.2F3), anti-CD122 FITC (TM-131), anti-Fas biotin (Jo2), anti-Fas ligand biotin (MFL3), streptavidin-PE, and streptavidin-allophycocyanin. Anti-BTLA PE (6F7) and anti-BTLA Alexa Fluor 647 (8F4) were purchased from eBioscience (San Diego, Calif.). After Fc receptors were blocked with anti-CD16/32 mAb (BD Biosciences), cells were stained with indicated antibodies and analyzed on a FACSCalibur (Becton Dickinson) using CellQuestPro software (Becton Dickinson).

Preparation of allophycocyanin-conjugated α-GalCer/CD1d-dimer: Allophycocyanin-conjugated α-GalCer/CD1d-dimer was prepared as described previously (22). In brief, 2.75 ml of α-GalCer (200 mg/ml) (Kirin Pharma Co. Ltd, Tokyo, Japan) and 6 ml of mouse CD1d-Ig fusion protein (0.5 mg/ml) (BD Biosciences) was conjugated at 37° C. overnight. The α-GalCer/CD1d-Ig conjugates were then incubated with allophycocyanin-conjugated anti-mouse IgG1 (X56; BD Biosciences) for 60 minutes. Free allophycocyanin-conjugated anti-mouse IgG1 in the mixture was blocked by the addition of excess amounts of control mouse IgG1 mAb (A111-3; BD Biosciences) for 30 minutes at room temperature.

Preparation of mononuclear cells from the liver: Liver was removed from mice after perfusion through portal vein and inferior vena cava with PBS. The liver was cut into small pieces, passed through a stainless steel mesh, and suspended in RPMI1640 medium for 3 minutes. Mononuclear cells were then harvested from the supernatants and enriched by Percoll (GE Healthcare UK Ltd., Little Chalfont, UK) gradient centrifugation according to the manufacturer's instruction.

Preparation of intrahepatic NKT cells by MACS: Liver mononuclear cells were incubated with anti-CD16/32 to block non-specific binding and then stained with a mixture of FITC-conjugated antibodies against B220, CD8α, CD11b, and CD11c, and allophycocyanin-conjugated α-GalCer/CD1d dimer. FITC-positive cells were depleted using anti-FITC MicroBeads (Miltenyi Biotec, Bergisch Gladbach, Germany) according to the manufacturer's protocol. Remaining cells were then incubated with anti-allophycocyanin MicroBeads (Miltenyi Biotec) and allophycocyanin-positive cells were positively collected twice by magnet cell sorting. The purity of collected cells was determined by flow cytometry and were routinely >95% of TCR-β$^+$ α-GalCer$^+$ cells.

Co-culture of NKT cells and α-GalCer-loaded cells: α-GalCer-loaded cells were prepared as described elsewhere (22) with a minor modification. In brief, single cell suspension of splenocytes was irradiated (30 gray) and incubated with α-GalCer (10 or 100 ng/ml) in complete RPMI 1640 medium (RPMI 1640 medium supplemented with 10% heat-inactivated FCS, 5.5 μM β-mercaptoethanol, 2 mM L-glutamine, nonessential amino acids, and antibiotics) for 12 hours. Hepatic NKT cells ($5 \times 10^4$) were enriched by MACS as described above and were co-cultured with α-GalCer loaded cells ($5 \times 10^4$) in complete RPMI1640 medium in 96-well round bottom plates for 36 hours.

Concanavalin A-induced hepatitis: Concanavalin A (ConA, Sigma-Aldrich) was dissolved in pyrogen-free PBS and injected to mice intravenously (10 or 20 mg/kg). Sera were collected from the individual mice at the indicated time after ConA injection. The levels of alanine aminotransferase (ALT) and aspartate aminotransferase (AST) in serum were measured by standard protocols (SRL, Tokyo, Japan).

Measurement of cytokine levels by ELISA: The levels of TNF-α, IL-4, and IFN-γ in the sera and the supernatants were measured by ELISA kits according to the manufacturer's protocols (TNF-α and IL-4 kits from BD Biosciences and IFN-γ kit from R&D Systems, Minneapolis, Minn.). The minimum significant value of the assay was 15 μg/ml of TNF-α and IL-4 and 30 pg/ml of IFN-γ.

Statistical analysis: Data are summarized as mean ±SD. The statistical analysis of the results was performed by the unpaired t-test. p values <0.05 were considered significant.

BTLA is Expressed On NKT Cells but is Dispensable for the Development and Maintenance of NKT Cells To determine whether BTLA is involved in the development and function of NKT cells, we first examined the expression of BTLA on NKT cells. Mononuclear cells from thymus, spleen, and liver in C57BL/6 mice were stained with anti-BTLA mAb (6F7) and the expression levels of BTLA on each cell type were evaluated by flow cytometry. As shown in FIG. 1, the expression of BTLA was detected on NKT cells, which were defined as CD3$^+$ α-GalCer/CD1d-dimer$^+$ cells, at the levels similar to those on CD3$^+$ T cells. Consistent with previous reports (3, 6), BTLA was expressed at higher levels on B220$^+$ B cells and at lower levels on NK cells (FIG. 1).

Figure 2:
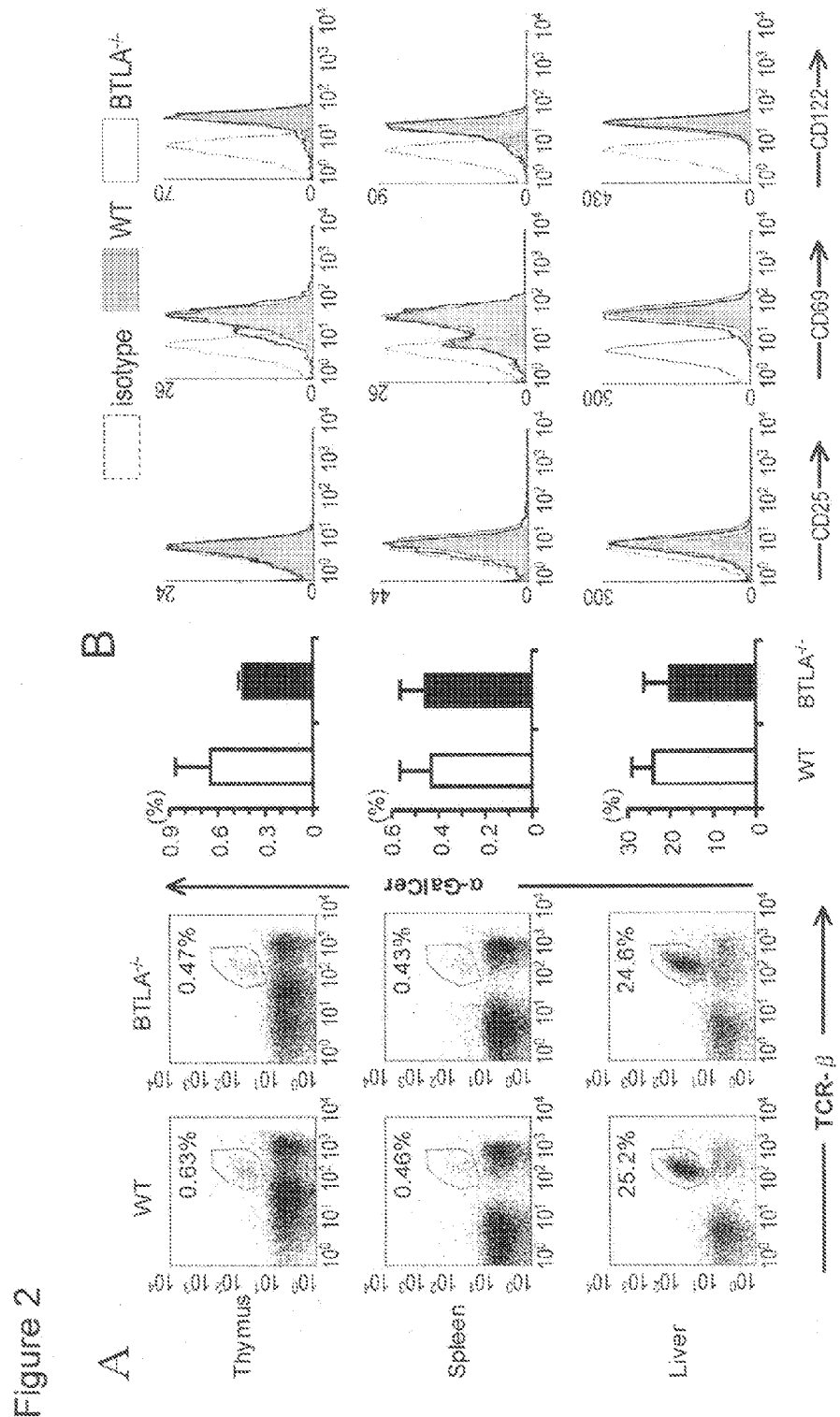
FIG. 2A shows representative FACS profiles of TCR-β vs. α-GalCer/CD1d-dimer staining (left panels) and the percentages of TCR-β$^+$ α-GalCer/CD1d-dimer$^+$ cells (right panels).
FIG. 2B shows representative histograms for CD25, CD69, and CD122 expression on TCR-β$^+$ α-GalCer/CD1d-dimer$^+$ cells (n=4 mice in each genotype). Normal development of NKT cells in BTLA$^{-/-}$ mice is reflected. Mononuclear cells from thymus, spleen, and liver in WT mice and BTLA$^{-/-}$ mice were stained with anti-TCR-β PE, allophycocyanin-conjugated α-GalCer/CD1d-dimer, and FITC-conjugated antibodies against CD25, CD69, or CD122 and analyzed by flow cytometry. Data are means ±SD for 4 mice in each genotype. Dotted lines indicate control staining with isotype-matched antibody.

We next examined the development and activation state of NKT cells in BTLA$^{-/-}$ mice. As previously demonstrated (3), the numbers of thymocytes and splenocytes in BTLA$^{-/-}$ mice at 8 weeks of age were comparable to those in wild-type (WT) mice (data not shown). Flow cytometric analysis revealed that the frequencies of NKT cells (TCRβ$^+$ α-GarCer/CD1d$^+$ cells) in thymus and spleen of BTLA$^{-/-}$ mice were comparable with those in WT mice (FIG. 2A). The number of NKT cells in the liver of BTLA$^{-/-}$ mice was also similar to that in WT mice (FIG. 2A). In addition, the expression levels of activation markers such as CD25, CD69, and CD122 on NKT cells were similar between BTLA$^{-/-}$ mice and WT mice (FIG. 2B). Together, these results indicate that BTLA is dispensable for the development and the maintenance of steady state of NKT cells.

BTLA-Deficient NKT Cells are Hyperreactive to Antigen Stimulation In Vitro

We next examined whether BTLA regulated NKT cell function. Purified NKT cells from the liver of WT mice and BTLA$^{-/-}$ mice were stimulated with α-GalCer-loaded APCs for 36 hours and the levels of IFN-γ and IL-4 in the culture supernatants were measured by ELISA (FIG. 3). In response to α-GalCer stimulation (100 ng/ml), BTLA$^{-/-}$ NKT cells secreted significantly larger amounts of IFN-γ and IL-4 as compared with WT NKT cells (IFN-γ: BTLA$^{-/-}$ 14.9±7.9 vs. WT 3.7±2.5 ng/ml, n=6, p<0.05) (IL-4: BTLA$^{-/-}$ 1.8±0.5 vs. WT 1.0±0.4 ng/ml, n=6, p<0.05). These results indicate that BTLA$^{-/-}$ NKT cells are hyperreactive to antigenic stimulation, suggesting that BTLA functions as an inhibitory co-receptor in NKT cell activation.

BTLA$^{-/-}$ Mice are Highly Susceptible to Concanavalin A-Induced Hepatitis

Concanavalin A (ConA)-induced hepatitis is a widely utilized mouse model that resembles autoimmune hepatitis in humans in many aspects (23). The development of hepatitis after ConA injection has been shown to be attenuated in the mice lacking NKT cells (19, 20), indicating that NKT cells are involved in causing ConA-induced hepatitis. We therefore chose this model to test the function of BTLA expressed on NKT cells in vivo. Importantly, when WT mice and BTLA$^{-/-}$ mice were injected intravenously with ConA (20 mg/kg), all BTLA$^{-/-}$ mice died by 24 hours after injection, whereas all WT mice survived over 48 hours (FIG. 4A). These results indicate that BTLA$^{-/-}$ mice are highly susceptible to ConA-induced hepatitis.

To examine the immune responses to ConA in BTLA$^{-/-}$ mice in detail, we utilized a sublethal dose of ConA (10 mg/kg) for BTLA$^{-/-}$ mice in the following experiments. First, we performed histological examination of the liver of ConA-injected BTLA$^{-/-}$ mice and WT mice. As shown in FIG. 4B, liver sections from ConA-injected BTLA$^{-/-}$ mice showed a massive necrosis and mononuclear cell infiltration in the portal area. In addition, the levels of alanine aminotransferase (ALT) and aspartate aminotransferase (AST) in sera of BTLA$^{-/-}$ mice were significantly elevated as compared with those of WT mice at 12 and 24 hours after ConA injection (n=6, *p<0.05, **p<0.01) (FIG. 4C), confirming the increased susceptibility to ConA-induced hepatitis in BTLA$^{-/-}$ mice.

BTLA-Deficient NKT Dells are Hyperreactive to Antigen Stimulation In Vitro

A number of studies have suggested a proinflammatory role of TNF-α, IFN-γ, and IL-4 and a protective role of IL-10 in the ConA-induced hepatitis (24-26). It has also been demonstrated that IL-4 produced by NKT cells is implicated in liver damage in ConA-induced hepatitis (19, 27). Therefore, we measured cytokine levels in sera of ConA-injected BTLA$^{-/-}$ mice and WT mice. The levels of TNF-α and IFN-γ showed a sharp increase in ConA-injected BTLA$^{-/-}$ mice and the peaks were higher than those in WT mice (FIG. 4D). The levels of TNF-α and IFN-γ reverted to the baseline at 24 hours after ConA injection in WT mice, but remained elevated in BTLA$^{-/-}$ mice (FIG. 4D). ConA-injected BTLA$^{-/-}$ mice also exhibited prolonged IL-4 production as compared with WT mice (FIG. 4D). On the other hand, the levels of IL-10 were comparable between ConA-injected BTLA$^{-/-}$ mice and WT mice (data not shown).

It has been reported that hepatic NKT cells rapidly up-regulates FasL expression on the surface and induces apoptosis of hepatocytes upon ConA stimulation (19, 20). We therefore examined FasL expression on hepatic NKT cells in ConA-injected BTLA$^{-/-}$ mice and WT mice. As shown in FIG. 4E, FasL was up-regulated on NKT cells but not on T cells or NK cells at 1 hour after ConA injection in both BTLA$^{-/-}$ mice and WT mice and the levels of FasL on NKT cells were similar between BTLA$^{-/-}$ mice and WT mice, suggesting that FasL expressed on NKT cells could not account for the enhanced susceptibility to ConA-induced hepatitis in BTLA$^{-/-}$ mice.

BTLA$^{-/-}$ Mice are Highly Susceptible to Concanavalin A-Induced Hepatitis

Concanavalin A (ConA)-induced hepatitis is a widely utilized mouse model that resembles autoimmune hepatitis in humans in many aspects (23). The development of hepatitis after ConA injection has been shown to be attenuated in the mice lacking NKT cells (19, 20), indicating that NKT cells are involved in causing ConA-induced hepatitis. We therefore chose this model to test the function of BTLA expressed on NKT cells in vivo. Importantly, when WT mice and BTLA$^{-/-}$ mice were injected intravenously with ConA (20 mg/kg), all BTLA$^{-/-}$ mice died by 24 hours after injection, whereas all WT mice survived over 48 hours (FIG. 4A). These results indicate that BTLA$^{-/-}$ mice are highly susceptible to ConA-induced hepatitis.

To examine the immune responses to ConA in BTLA$^{-/-}$ mice in detail, we utilized a sublethal dose of ConA (10 mg/kg) for BTLA$^{-/-}$ mice in the following experiments. First, we performed histological examination of the liver of ConA-injected BTLA$^{-/-}$ mice and WT mice. As shown in FIG. 4B, liver sections from ConA-injected BTLA$^{-/-}$ mice showed a massive necrosis and mononuclear cell infiltration in the portal area. In addition, the levels of alanine aminotransferase (ALT) and aspartate aminotransferase (AST) in sera of BTLA$^{-/-}$ mice were significantly elevated as compared with those of WT mice at 12 and 24 hours after ConA injection (n=6, *p<0.05, **p<0.01) (FIG. 4C), confirming the increased susceptibility to ConA-induced hepatitis in BTLA$^{-/-}$ mice.

A number of studies have suggested a proinflammatory role of TNF-α, IFN-γ, and IL-4 and a protective role of IL-10 in the ConA-induced hepatitis (24-26). It has also been demonstrated that IL-4 produced by NKT cells is implicated in liver damage in ConA-induced hepatitis (19, 27). Therefore, we measured cytokine levels in sera of ConA-injected BTLA$^{-/-}$ mice and WT mice. The levels of TNF-α and IFN-γ showed a sharp increase in ConA-injected BTLA$^{-/-}$ mice and the peaks were higher than those in WT mice (FIG. 4D). The levels of TNF-a and IFN-γ reverted to the baseline at 24 hours after ConA injection in WT mice, but remained elevated in BTLA$^{-/-}$ mice (FIG. 4D). ConA-injected BTLA$^{-/-}$ mice also exhibited prolonged IL-4 production as compared with WT mice (FIG. 4D). On the other hand, the levels of IL-10 were comparable between ConA-injected BTLA$^{-/-}$ mice and WT mice (data not shown).

It has been reported that hepatic NKT cells rapidly up-regulates FasL expression on the surface and induces apoptosis of hepatocytes upon ConA stimulation (19, 20). We therefore examined FasL expression on hepatic NKT cells in ConA-injected BTLA$^{-/-}$ mice and WT mice. As shown in FIG. 4E, FasL was up-regulated on NKT cells but not on T cells or NK cells at 1 hour after ConA injection in both BTLA$^{-/-}$ mice and WT mice and the levels of FasL on NKT cells were similar between BTLA$^{-/-}$ mice and WT mice, suggesting that FasL expressed on NKT cells could not account for the enhanced susceptibility to ConA-induced hepatitis in BTLA$^{-/-}$ mice.

NKT Cells are Required for the Augmentation of ConA-Induced Hepatitis in BTLA$^{-/-}$ Mice To determine whether the augmentation of ConA-induced hepatitis in BTLA$^{-/-}$ mice depends on NKT cells, we examined the susceptibility to ConA-induced hepatitis in the mice lacking both BTLA and NKT cells (BTLA$^{-/-}$ NKT$^{-/-}$ mice). We first examined lymphocyte development in BTLA$^{-/-}$ NKT$^{-/-}$ mice and found that BTLA$^{-/-}$ NKT "*i*" mice lacked NKT cells but had normal numbers of other lymphoid populations (data not shown). We then compared the levels of ALT and AST in BTLA$^{-/-}$ NKT "*i*" mice, BTLA$^{-/-}$ mice, NKT mice, and WT mice upon ConA injection. Consistent with a previous study (19), ConA-induced hepatitis was significantly attenuated in NKT mice as compared with WT mice (FIG. 5), indicating that NKT cells play an important role in causing ConA-induced hepatitis. Importantly, the augmentation of ConA-induced hepatitis in BTLA$^{-/-}$ mice was not observed in BTLA$^{-/-}$ NKT mice (FIG. 5). Histological analysis confirmed the reduced liver damage in ConA-injected BTLA$^{-/-}$ NKT mice as compared with BTLA$^{-/-}$ mice (data not shown). These results indicate that NKT cells are critical for the augmentation of ConA-induced hepatitis in BTLA$^{-/-}$ mice.

NKT Cells are Required for the Augmentation of ConA-Induced Hepatitis in BTLA$^{-/-}$ Mice.

To determine whether the augmentation of ConA-induced hepatitis in BTLA$^{-/-}$ mice depends on NKT cells, we examined the susceptibility to ConA-induced hepatitis in the mice lacking both BTLA and NKT cells (BTLA$^{-/-}$ NKT$^{-/-}$ mice). We first examined lymphocyte development in BTLA$^{-/-}$ NKT mice and found that BTLA$^{-/-}$ NKT mice lacked NKT cells but had normal numbers of other lymphoid populations (data not shown). We then compared the levels of ALT and AST in BTLA$^{-/-}$ NKT mice, BTLA$^{-/-}$ mice, NKT$^{-/-}$ mice, and WT mice upon ConA injection. Consistent with a previous study (19), ConA-induced hepatitis was significantly attenuated in NKT$^{-/-}$ mice as compared with WT mice (FIG. 5), indicating that NKT cells play an important role in causing ConA-induced hepatitis. Importantly, the augmentation of ConA-induced hepatitis in BTLA$^{-/-}$ mice was not observed in BTLA$^{-/-}$ NKT mice (FIG. 5). Histological analysis confirmed the reduced liver damage in ConA-injected BTLA$^{-/-}$ NKT$^{-/-}$ mice as compared with BTLA$^{-/-}$ mice (data not shown). These results indicate that NKT cells are critical for the augmentation of ConA-induced hepatitis in BTLA$^{-/-}$ mice.

Example 2

The materials and methods used for Example 2 are described below:

Mice. BTLA-deficient (BTLA$^{-/-}$) mice were established on a 129SvEv background as described previously (3) and their offsprings were backcrossed into MRL-lpr/lpr mice for eight generations to generate BTLA-deficient mice on MRL-lpr/lpr background. Wild-type MRL-lpr/lpr mice were purchased from Takasugi Laboratory Animal Corp (Saitama, Japan). Mice were housed in microisolator cages under specific pathogen-free conditions. All experiments were performed according to the guidelines of Chiba University.

Antibodies. The following antibodies were purchased from BD PharMingen (San Diego, Calif.): anti-CD3ε biotin, PE (145-2C11), anti-CD4 FITC, PE (L3T4, RM4-5), anti-CD8α FITC, PE, Cy-chrome (Ly-2, 53-6.7), anti-CD25 biotin (PC61), anti-CD45R/B220 FITC, PE (RA3-6B2), anti-CD69 FITC (H1.2F3), anti-CD62L PE (MEL-14), anti-Ly-6G/C PE (Gr-1), anti-CD11b (Mac-1) PE (M1/70), anti-CD49b/Pan-NK PE (DX5), and APC-Streptavidin (SA).

Flow cytometric analysis Single cell suspensions of thymocytes, splenocytes, and mononuclear cells in the liver were obtained from 4-month-old BTLA$^{-/-}$ MRL-lpr/lpr mice and littermate BTLA WT MRL-lpr/lpr mice. The mononuclear cells in the liver were separated by Ficoll gradient fractionation. The cells ($1\times10^6$) were washed twice, stained with antibodies described above, and analyzed on a FACSCalibur (Becton Dickinson, Mountain View, Calif.) using CELL Quest™ software (Becton Dickinson). Prior to staining, Fc receptors were blocked with anti-CD 16/32 antibody (2.4G2, BD PharMingen).

Histopathology and immunohistochemistry. Tissues were fixed in 4% paraformaldehyde in phosphate-buffered saline (PBS) and embedded in paraffin. Sections (4 ptm thick) were stained with hematoxylin and eosin (HE) and examined by microscopy. Liver sections were also stained with reticulum fiber silver stain by standard protocols. Kidney sections were stained with periodic acid methenamine silver (PAM) stain and periodic-acid Schiff (PAS). For immunohistochemistry, tissues were embedded in OCT compound (Sakura, Torrance, Calif.). Cryosections (5 gm thick) were fixed in cold acetone, blocked with normal rabbit serum for 20 min at room temperature, and incubated with biotinylated antibodies against mouse CD3E, CD45R/B220, CD4, CD8α, Ly-6G/C (Gr-1), and CD11b (Mac-1α) for 90 min at room temperature. Biotinylated antibodies against hamster IgG or rat IgG2 were used as controls. After washing twice with PBS, sections were incubated with avidin and biotinylated-horseradish peroxidase (Funakoshi, Tokyo, Japan) and developed with 0.02% $H_2O_2$ and diaminobenzidine tetrahydrochloride (Dako Cytomation, Kyoto, Japan) according to the manufacturer's instruction. The sections were counterstained with hematoxylin by standard protocols.

Biochemical analysis of sera. Sera were collected from individual BTLA$^{-/-}$ MRL-lpr/lpr mice and littermate BTLA WT MRL-lpr/lpr mice at 4 months of age. The levels of asparate aminotransferase (AST), alanine aminotransferase (ALT), γ-glutamic transpeptidase (γ-GTP), alkaline phosphatase (ALP), total bilirubin (T-Bil), and blood urea nitrogen (BUN) were determined by standard protocols (SRL, Inc., Tokyo, Japan).

Statistical analysis. Data are summarized as mean ±SD. The unpaired t-test was used for statistical analysis. P values less than 0.05 were considered significant.

BTLA$^{-/-}$ MRL-lpr/lpr mice developed marked splenomegaly and showed lpr cell accumulation in the spleen. We compared the survival rate of BTLA$^{-/-}$ MRL-lpr/lpr mice and littermate BTLA wild-type (WT) MRL-lpr/lpr mice. BTLA.$^{-/-}$ MRL-lpr/lpr mice had a significant reduction in the survival rate compared with WT MRL-lpr/lpr mice (log-rank test, p<0.05) (Wilcoxon rank sum test, p<0.01). The overall 5 months survival rates for BTLA WT MRL-lpr/lpr mice and BTLA$^{-/-}$ MRL-lpr/lpr mice were 75% and 32%, respectively (FIG. 6A).

Figure 6B:
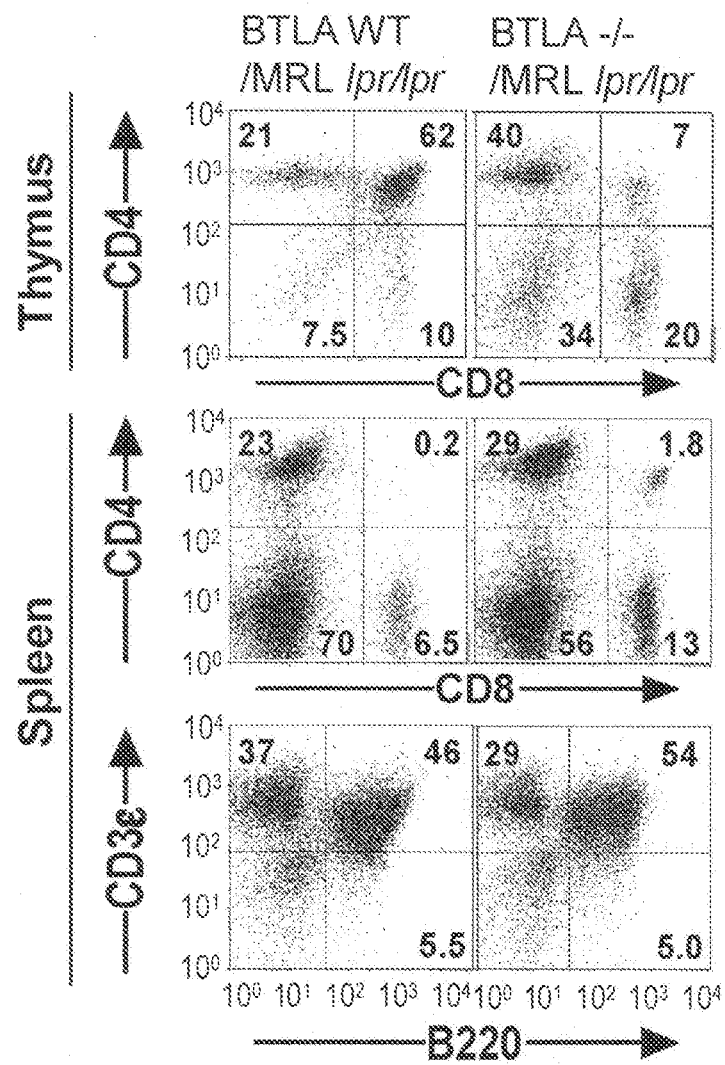
FIG. 6B shows Lymphocyte subpopulations in the thymus and spleen of BTLA$^{-/-}$ MRL-lpr/lpr mice. Thymocytes from 4-month-old BTLA$^{-/-}$ MRL-lpr/lpr mice and BTLA WT MRL-lpr/lpr mice were stained for CD4 and CD8 and analyzed by flow cytometry. Splenocytes were also stained for CD4 and CD8 or CDR and B220.
Figure 6C:
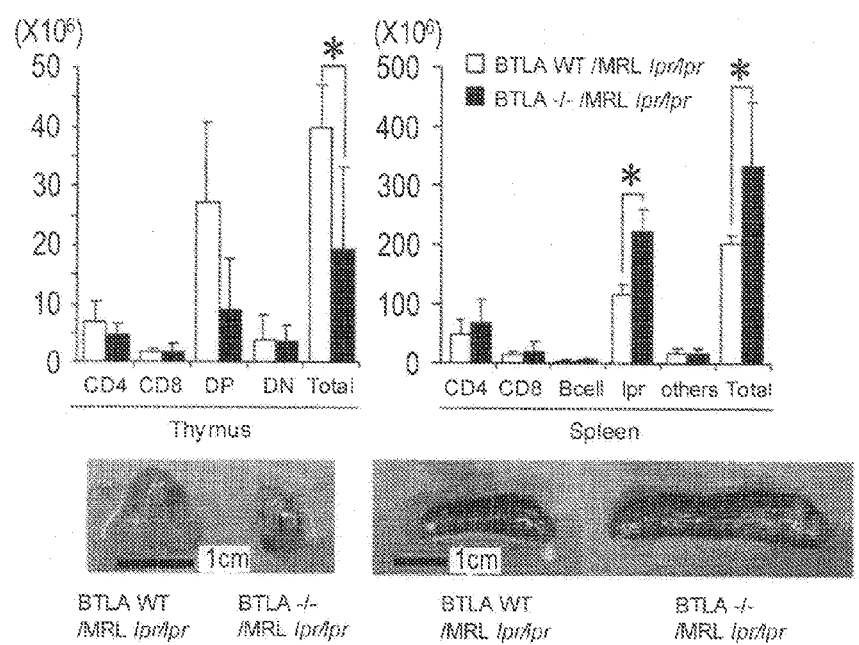
FIG. 6 A shows survival rates of BTLA$^{-/-}$ MRL-lpr/lpr mice and littermate BTLA WT MRL-lpr/lpr mice, reflecting exacerbation of splenomegaly and short life span in BTLA$^{-/-}$ MRL-lpr/lpr mice.
(A) BTLA$^{-/-}$ MRL-lpr/lpr mice (bold line; n=29) and littermate BTLA WT MRL-lpr/lpr mice (thin line; n=36) were bred under specific pathogen-free conditions. The lifespan of BTLA$^{-/-}$ MRL-lpr/lpr mice is significantly shorter than that of BTLA WT MRL-lpr/lpr mice, p<0.05 (log-rank test).

To define the role of BTLA in the progression of autoimmunity in MRL-lpr/lpr mice, we first measure the levels of splenomegaly in BTLA$^{-/-}$ MRL-lpr/lpr mice and BTLA WT MRL-lpr/lpr mice. The Spleens of BTLA$^{-/-}$ MRL-lpr/lpr mice at 4 months of age were significantly large in size and in weight. The number of splenocytes in BTLA$^{-/-}$ mice was also significantly increased as compared with that in BTLA WT MRL-lpr/lpr mice by approximately 66% (WT mice 201±10 vs. BTLA$^{-/-}$ mice 335±104×10$^6$, n=5, p<0.05) (FIG. 6B, C). FACS analysis revealed that the numbers of lpr cells (CD3ε$^+$ B220$^+$) was significantly increased in the BTLA$^{-/-}$ MRL-lpr/lpr mice as compared with that in BTLA WT MRL-lpr/lpr mice (WT mice 118±18.5 vs. BTLA$^{-/-}$ mice 225±4.7×10$^6$, n=5, p<0.05)

We then analyzed thymocyte development in BTLA$^{-/-}$ MRL-lpr/lpr mice to test whether the abnormal thymocyte development is involved in the exaggeration of splenomegaly and in the increase of lpr cells. Although the numbers of CD4$^+$ CD8$^-$ single-positive, CD4$^-$ CD8$^+$ single-positive and CD4$^-$ CD8$^-$ (double negative, DN) thymocytes in 4-months-old BTLA$^{-/-}$ MRL-lpr/lpr mice were similar to those of BTLA WT MRL-lpr/lpr mice, the total number of thymocytes in BTLA$^{-/-}$ mice was significantly smaller as compared with that in WT MRL lpr/lpr mice by approximately 50% (WT mice 53±6.9 vs. BTLA$^{-/-}$ mice 28±13.7×10$^6$, n=4, p<0.05) (FIG. 6B, C). Major cause of this decrease of total thymocytes is due to the decrease of CD4$^+$ CD8$^+$ (double positive, DP) thymocytes. We next analyzed the expression levels of CD3ε and CD69 during the thymocyte development. These positive/maturation markers were normally up-regulated in BTLA$^{-/-}$ MRL-lpr/lpr mice as compared with BTLA WT MRL-lpr/lpr mice (data not shown).

Figure 7:
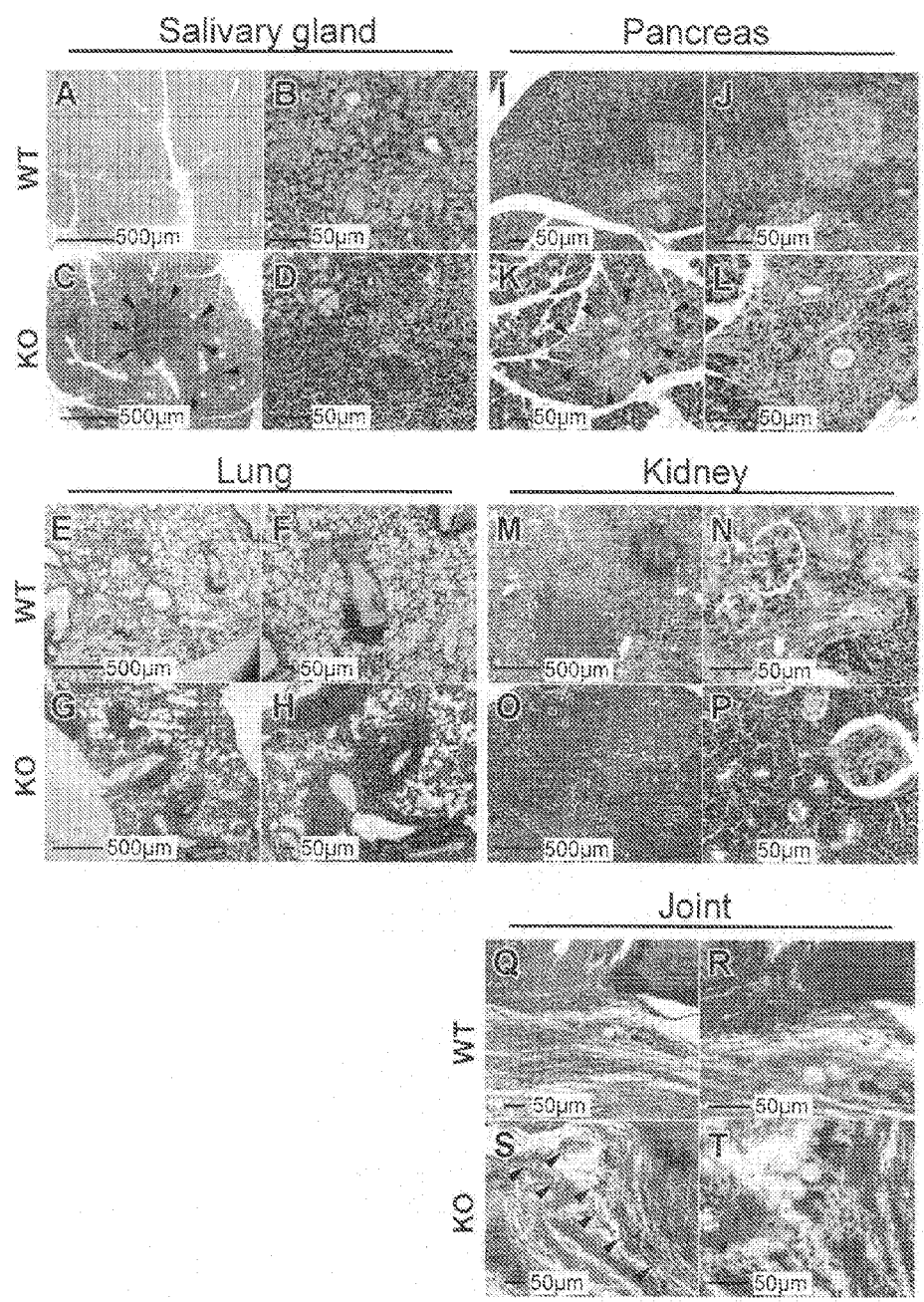
FIGS. 7 A-D show representative photographs of hematoxylin and eosin staining (HE) of salivary gland of 4-month-old BTLA$^{-/-}$ MRL-lpr/lpr mice and BTLA WT MRL-lpr/lpr mice, reflecting exacerbation of inflammatory cell infiltration in multiple organs of BTLA$^{-/-}$ MRL-lpr/lpr mice. Figures C and D show massive inflammatory cell infiltration in the salivary glands of BTLA$^{-/-}$ MRL-lpr/lpr mice.

Spontaneous development of massive inflammatory cell infiltrates in multiple organs in BTLA MRL-lpr/lpr mice. MRL-lpr/lpr mice are known to develop lupus-like diseases and lymphoproliferative changes in lung, kidney, salivary gland and joints. We perform the histological examination of these organs. As shown in FIG. 7, massive inflammatory cell infiltrations that mainly consisted of lymphocytes were found in tissue sections of salivary glands of 4-month-old BTLA$^{-/-}$ MRL-lpr/lpr mice. The size of the inflammatory foci and the number of infiltrating cells in salivary glands in BTLA$^{-/-}$ MRL-lpr/lpr mice are larger than those in BTLA WT MRL-lpr/lpr mice (FIG. 7A-D).

Inflammatory cell infiltration around the bronchus in the lung is the most common lung involvement in MRL-lpr/lpr mice. We also found a week level of lung involvements in 4-month-old BTLA WT MRL-lpr/lpr mice (FIG. 7E, F), but the size and the number of inflammatory cell infiltration are also obviously larger in the lung of BTLA$^{-/-}$ MRL-lpr/lpr mice (FIG. 7G, H).

Lymphocyte infiltration in the pancreas is also reported in MRL lpr/lpr mice. We could detect lymphocyte infiltration in the pancreas in only 1 out of 5 BTLA WT MRL-lpr/lpr mice (FIG. 7I, J). But we detected massive lymphoproliferative invasions in pancreas in all (5/5) BTLA$^{-/-}$ MRL-lpr/lpr mice (FIG. 7K, L).

Glomerulonephritis and interstitial nephritis are common pathological findings in MRL-lpr/lpr mice (FIG. 7M,N). The size and the number of infiltration in kidneys of BTLA$^{-/-}$ MRL-lpr/lpr mice are larger than those in BTLA WT MRL-lpr/lpr mice (FIG. 7O, P).

Mononuclear cell infiltration in joints is spontaneously developed in MRL lpr/lpr mice. Mild infiltrations in 1 out of 5 BTLA WT MRL lpr/lpr mice (FIG. 7Q, R)was observed, but moderate to severe lymphocyte invasions in knee joint in 4 out of 5 BTLA$^{-/-}$ MRL-lpr/lpr mice was observed (FIG. 7S, T).

Figure 8:
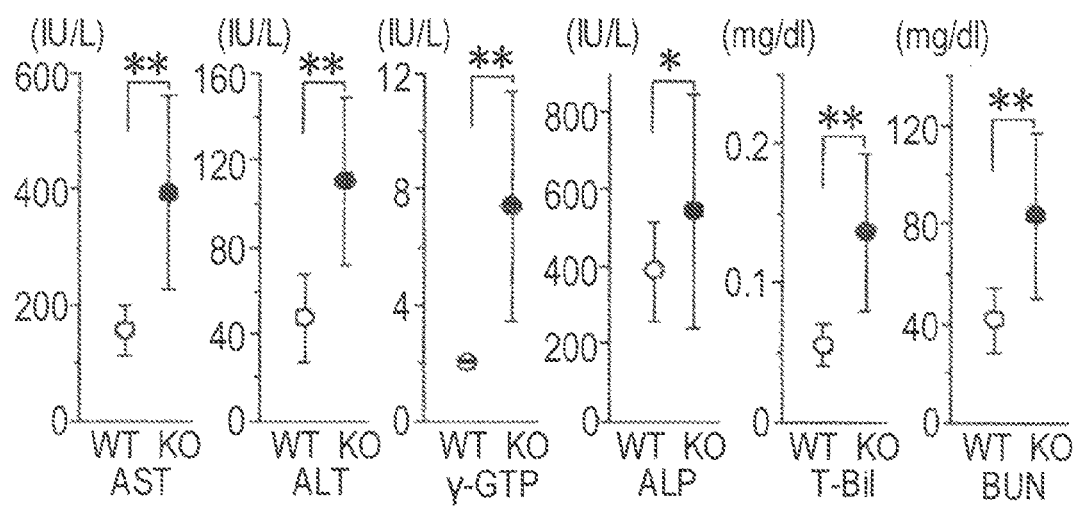
FIG. 8 shows of AST, ALT, γ-GTP, ALP, T-Bil, and BUN, reflecting exacerbation of liver and renal dysfunction in BTLA$^{-/-}$ MRL-lpr/lpr mice (A) Sera were collected from BTLA$^{-/-}$ MRL-lpr/lpr mice and BTLA WT MRL-lpr/lpr mice (BTLA$^{-/-}$ mice: n=21, WT mice: n=17) at 4 months of age and the levels of AST, ALT, γ-GTP, ALP, T-Bil, and BUN were determined. Circles indicate the mean titer of each group. All serum levels of liver or renal dysfunction markers are significantly higher in BTLA$^{-/-}$ MRL-lpr/lpr mice than those in BTLA WT MRL-lpr/lpr mice. *p<0.05, **p<0.01.

Spontaneous development of autoimmune hepatitis-like disease in BTLA$^{-/-}$ MRL-lpr/lpr mice. Blood serum tests of BTLA$^{-/-}$ MRL-lpr/lpr mice at 4 months of age also showed the significant elevation of liver damage markers such as asparate aminotransferase (AST), alanine aminotransferase (ALT), γ-glutamic transpeptidase (γ-GTP), alkaline phosphatase (ALP), and total bilirubin (T-Bil) (FIG. 8).

Figure 9:
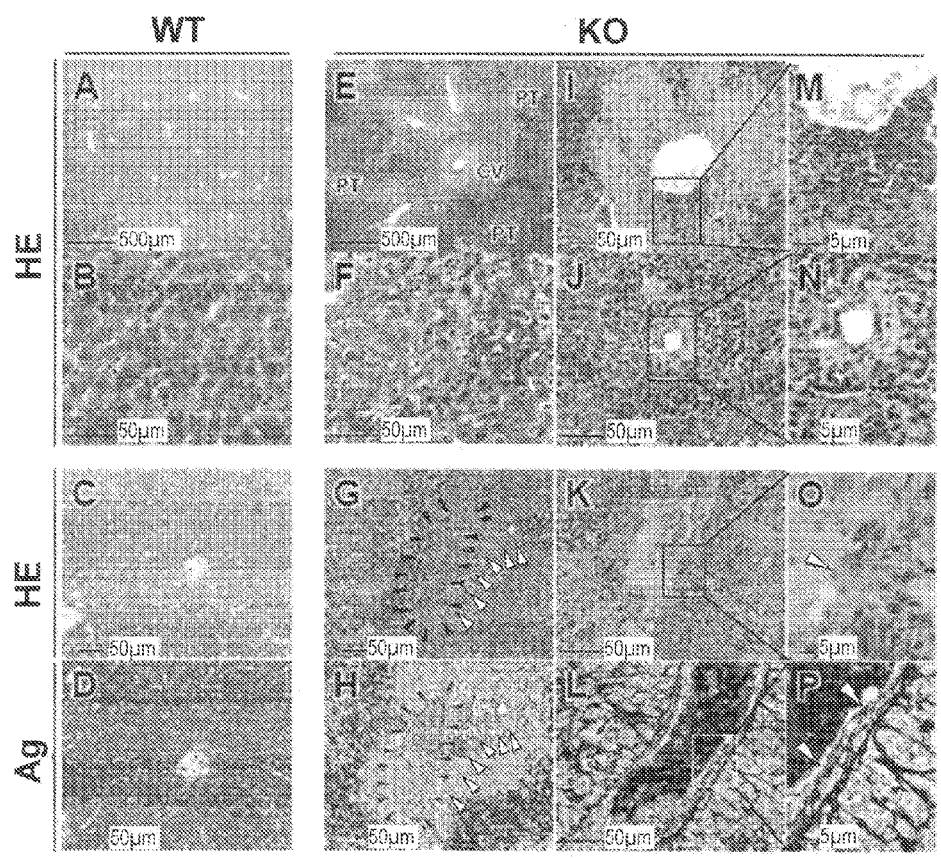
FIG. 9 A-D shows representative photographs of HE staining or silver staining (Ag) of the liver sections from 4-month-old BTLA WT MRL-lpr/lpr (A-D) and BTLA$^{-/-}$ MRL-lpr/lpr mice (E-P) are shown, reflecting spontaneous development of autoimmune hepatitis-like disease in BTLA$^{-/-}$ MRL-lpr/lpr mice.

We next examined the organs histologically in BTLA$^{-/-}$ MRL-lpr/lpr mice. Interestingly, although the liver is not susceptible to inflammatory cell infiltration in BTLA WT MRL-lpr/lpr mice (FIG. 9A-D), livers in BTLA$^{-/-}$ MRL-lpr/lpr mice showed prominent inflammatory changes. Liver sections from BTLA$^{-/-}$ MRL-lpr/lpr mice showed severe mononuclear cell infiltration mainly in the portal tract (FIG. 9E) and also in the lobules (FIG. 9F). Mononuclear cell infiltration in the portal tracts disrupted the limiting plate and penetrated into the periportal hepatic lobules (FIG. 9G, H). This inflammatory cell infiltration extending into the adjacent parenchyma (interface hepatitis or piecemeal necrosis) is thought to be a hallmark of autoimmune hepatitis (AIH) in humans.

Liver section of BTLA$^{-/-}$ MRL-lpr/lpr mice also showed the prominent subendothelial mononuclear cell infiltration in the portal and hepatic veins that resulted in the detachment of the endothelial cells from the basement membrane (endothelialitis) (FIG. 9K, O). Inflammatory cell infiltrates were predominantly composed of blastic lymphocytes and an affluent number of plasma cells with occasional eosinophils and neutrophils. In addition to portal areas, a part of penetrating inflammatory cells to the lobule reached the central veins (FIG. 9I, M). Hepatocytes around the central veins were severely damaged by infiltrating inflammatory cells and presumably by an ischemia due to the prominent portal inflammation. Bile ducts were also damaged by severe inflammation in the portal tracts. These findings suggest that the damage of veins and bile ducts in the Glisson's sheath is induced by immune dysregulation in the liver.

Figure 10:
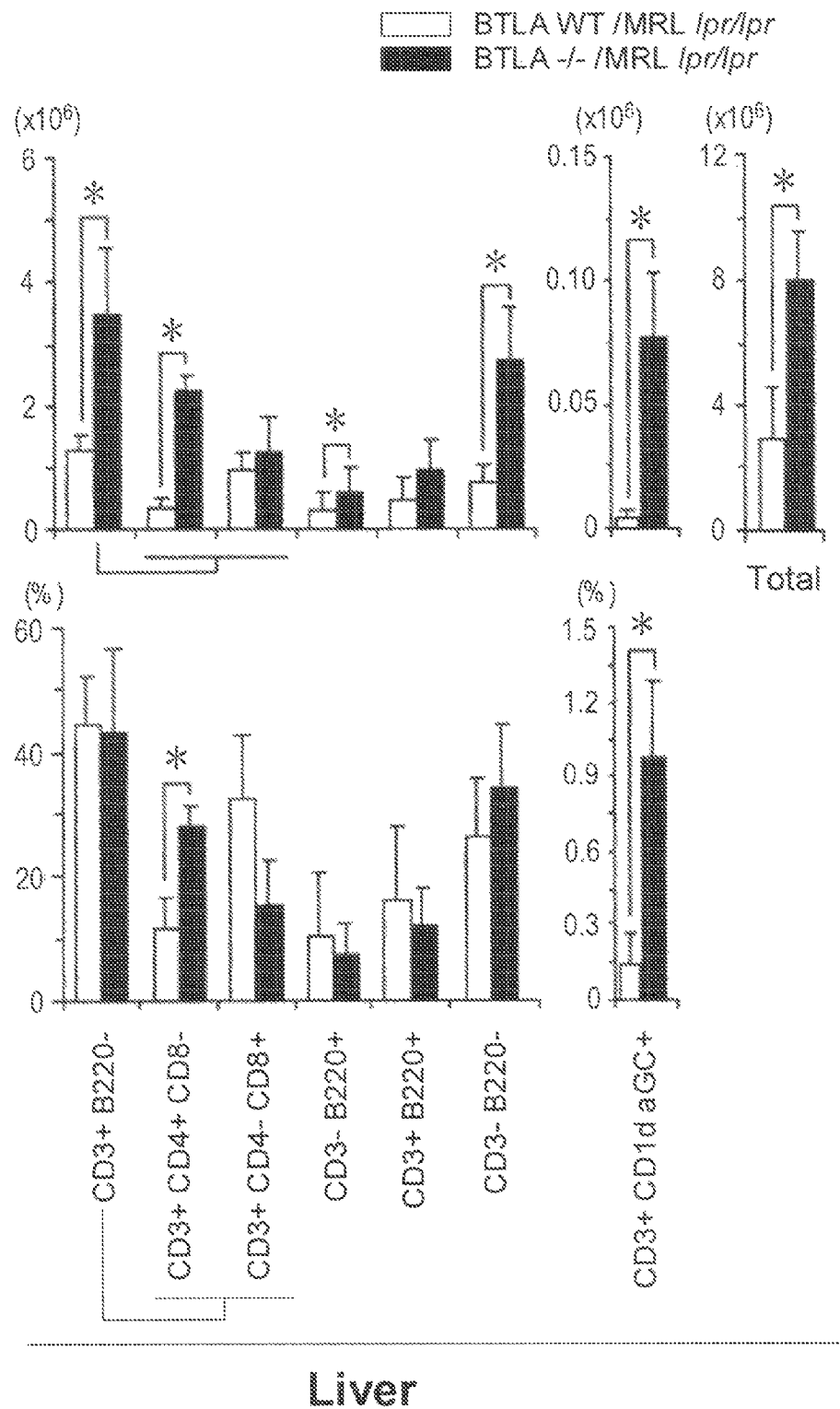
FIG. 10 shows flow cytometric analysis of liver infiltrates in BTLA$^{-/-}$ MRL-lpr/lpr mice. Mononuclear cells were separated from the liver of 4 month-old BTLA$^{-/-}$ MRL-lpr/lpr mice and littermate BTLA WT MRL-lpr/lpr mice by Ficoll gradient fractionation, stained with antibodies against CD3ε, B220, CD4, CD8, and CD1d dimer-αGalCer, and then analyzed by flow cytometry. The numbers and percentages of T cells (CD3ε$^+$ B220$^-$), CD4$^+$T cells (CD3ε$^+$ CD4$^+$ CD8$^-$), CD8$^+$ T cells (CD3ε$^+$ CD4$^-$ CD8$^+$), lpr cells (CD3ε$^+$ B220$^+$), B cells (CD3ε$^-$ B220$^+$), other cells (CD3ε$^-$ B220$^-$), NK T cells (CDR$^+$ CD1d dimer-αGalCer$^+$) are show. Data are mean ±SD for 4 mice in each group, *p<0.05.

CD4$^+$ T cells and NK T cells are increased in the liver of BTLA$^{-/-}$ MRL-lpr/lpr mice. To further investigate the immunological dysregulation causing the liver damage in BTLA$^{-/-}$ MRL-lpr/lpr mice, we examined infiltrating cells in the liver of 4-month-old BTLA$^{-/-}$ MRL-lpr/lpr mice. As shown in FIG. 10, the total number of infiltrating cells in the liver of BTLA$^{-/-}$ MRL-lpr/lpr mice was significantly higher than those of BTLA WT MRL-lpr/lpr mice (2.9±1.6 vs. 8.0±1.6,× 10$^6$, n=4). Among them, the number and the frequency of CD4$^+$ T cells and NK T cells (CD3ε$^+$ CD1d-αGalCel$^+$) were significantly increased in BTLA$^{-/-}$ MRL-lpr/lpr mice. In contrast, the frequencies of CD8$^+$ T cells, B cells were not increased in the liver of BTLA$^{-/-}$ MRL-lpr/lpr mice. It has been demonstrated that NK T cells are responsible for the development of Concanavalin A (Con A)-induced hepatitis, which is considered to be a mouse model of AIH. We found that NK T cells of MRL lpr/lpr mice constitutively express BTLA (data not shown). It has also been demonstrated that HVEM-deficient mice exhibit increased morbidity and mortality in Con A-induced hepatitis as compared with WT mice. We also found that NK T cells from the liver of BTLA$^{-/-}$ mice produce higher IFN-γ and IL-4 after the stimulation of αGalCer (data not shown). These cytokines are thought to be necessary for the development of Con-A induced hepatitis.

Taken together, it is suggested that the deficiency of BTLA/HVEM interaction causes the increase of CD4$^+$ T cells and NK T cells in the liver and induces AIH-like disease in BTLA$^{-/-}$ MRL-lpr/lpr mice. However, the initial intrinsic stimuli for NK T cells in the liver of BTLA$^{-/-}$ MRL-lpr/lpr mice remain to be elucidated.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of identifying a compound for preventing and/or treating an autoimmune disease, comprising
    (1) obtaining a (BTLA$^{-/-}$) NKT cell from a non-human animal,
    (2) contacting the (BTLA$^{-/-}$) NKT cell ex vivo with a test compound, in the presence of an antigen,
    (3) measuring a response of the (BTLA$^{-/-}$) NKT cell to the antigen,
    (4) comparing the response of the (BTLA$^{-/-}$) NKT cell to the antigen with a response of a (BTLA$^{-/-}$) NKT cell in a control assay, and
    (5) selecting the compound that reduces the response of the (BTLA$^{-/-}$) NKT cell in the presence of an antigen compared to a response of a (BTLA$^{-/-}$) NKT cell in the control assay.

2. The method according to claim 1, wherein the non-human animal is a mouse.

3. The method according to claim 1, wherein the non-human animal is an MRL lpr/lpr mouse.

4. The method according to claim 1, wherein the measuring the response of the (BTLA$^{-/-}$) NKT cell to an antigen comprises measuring an increased cytokine production of the (BTLA$^{-/-}$) NKT cell that is contacted with the antigen.

5. The method according to claim 1, wherein the autoimmune disease is autoimmune hepatitis and the (BTLA$^{-/-}$) NKT cells are hepatic (BTLA$^{-/-}$) NKT cells.

6. A method of identifying a compound for preventing and/or treating an autoimmune disease, comprising
  (1) obtaining a (BTLA$^{-/-}$) NKT cell from a non-human animal,
  (2) contacting the (BTLA$^{-/-}$) NKT cell with a test compound, in the presence of an antigen under suitable assay conditions
  (3) measuring an increased cytokine production from the (BTLA$^{-/-}$) NKT cell in response to the antigen, and
  (4) selecting a compound that has an effect of reducing the increased cytokine production in comparison to a response of a (BTLA$^{-/-}$) NKT cell which has not been contacted with a compound.

7. The method according to claim 6, wherein the autoimmune disease is autoimmune hepatitis and the (BTLA$^{-/-}$) NKT cells are hepatic (BTLA$^{-/-}$) NKT cells.

8. The method according to claim 1, further comprising
  (i) administering the selected compound to a non-human animal that lacks at least a part of a BTLA gene,
  (ii) measuring a response of the non-human animal to a substance that causes an autoimmune response, and
  (iii) determining that the compound can prevent and/or treat the autoimmune disease when the compound causes a reduced or attenuated response to the antigen, compared to the response of a non-human animal to which the compound has not been administered.

9. A method of identifying a compound for preventing and/or treating an autoimmune disease, comprising
  (1) obtaining a (BTLA$^{-/-}$) NKT cell from a non-human animal,
  (2) contacting the (BTLA$^{-/-}$) NKT cell ex vivo with a test compound, in the presence of an antigen;
  (3) measuring a response of the (BTLA$^{-/-}$) NKT cell to the antigen; and
  (4) selecting a compound that has an effect of reducing the response to the antigen, in comparison to a response of a (BTLA$^{-/-}$) NKT cell in a control assay; and then
    (i) administering the selected compound to the non-human animal,
    (ii) measuring a response of the non-human animal to a substance that causes an autoimmune response, and
    (iii) determining that a compound prevents and/or treats the autoimmune disease when the compound causes reduced response of the (BTLA$^{-/-}$) NKT cells in response to the antigen, in comparison to a response of a non-human animal to which the test compound has not been administered.

10. A method of identifying a compound for inhibiting or reducing the response of a (BTLA$^{-/-}$) NKT cell to an antigen comprising:
  (1) obtaining a (BTLA$^{-/-}$) NKT cell from a non-human animal,
  (2) contacting the (BTLA$^{-/-}$) NKT cell ex vivo with a test compound, in the presence of the antigen,
  (3) measuring a response of the (BTLA$^{-/-}$) NKT cell to the antigen,
  (4) comparing the response of the (BTLA$^{-/-}$) NKT cell to the antigen with a response of a (BTLA$^{-/-}$) NKT cell in a control assay, and
  (5) selecting the compound that reduces the response of the (BTLA$^{-/-}$) NKT cell in the presence of an antigen compared to a response of a (BTLA$^{-/-}$) NKT cell in the control assay.

* * * * *